(12) United States Patent
Markle et al.

(10) Patent No.: US 7,947,968 B1
(45) Date of Patent: May 24, 2011

(54) PROCESSING SUBSTRATES USING DIRECT AND RECYCLED RADIATION

(75) Inventors: David A. Markle, Saratoga, CA (US); Shiyu Zhang, Hayward, CA (US)

(73) Assignee: Ultratech, Inc., San Jose, CA (US)

( * ) Notice: Subject to any disclaimer, the term of this patent is extended or adjusted under 35 U.S.C. 154(b) by 304 days.

(21) Appl. No.: 12/322,096

(22) Filed: Jan. 29, 2009

(51) Int. Cl.
*G01N 21/00* (2006.01)
*B23K 26/06* (2006.01)
*G03B 27/72* (2006.01)

(52) U.S. Cl. .............. 250/492.2; 250/492.1; 355/45; 430/298; 372/101; 372/38.02

(58) Field of Classification Search .............. 250/492.2, 250/492.1; 430/298; 355/45; 372/101, 38.02
See application file for complete search history.

(56) References Cited

U.S. PATENT DOCUMENTS

| | | | |
|---|---|---|---|
| 6,366,308 B1 | 4/2002 | Hawryluk et al. | |
| 6,531,681 B1 | 3/2003 | Markle et al. | |
| 6,747,245 B2 * | 6/2004 | Talwar et al. | 219/121.8 |
| 6,753,947 B2 * | 6/2004 | Meisburger et al. | 355/69 |
| 7,154,066 B2 * | 12/2006 | Talwar et al. | 219/121.8 |
| 7,298,496 B2 * | 11/2007 | Hill | 356/512 |
| 2005/0045604 A1 | 3/2005 | Talwar et al. | |
| 2005/0189329 A1 | 9/2005 | Talwar et al. | |

\* cited by examiner

*Primary Examiner* — Nikita Wells
(74) *Attorney, Agent, or Firm* — Allston L. Jones; Peters Verny, LLP

(57) ABSTRACT

Provided are apparatuses for processing a surface of a substrate using direct and recycled radiation reflected from the substrate. The apparatus includes a radiation source positioned to direct a radiation beam toward a beam image forming system that forms a beam image on the substrate surface and a recycling system. The recycling system collects radiation reflected from the substrate surface and redirects it back toward the beam image on the substrate in a +1× manner. As a result, radiation incident on and reflected from the substrate is recycled through multiple cycles. This improves the uniformity of the radiation absorbed by the substrate in instances where the thin film patterns on the substrate would otherwise result in non-uniform absorption and uneven heating. Exemplary recycling systems suitable for use with the invention include Offner and Dyson relay systems as well as variants thereof.

21 Claims, 15 Drawing Sheets

Section B-B

PROCESSING SUBSTRATES USING DIRECT AND RECYCLED RADIATION

BACKGROUND OF THE INVENTION

1. Field of the Invention

The present invention relates to apparatus and methods for processing a surface of a substrate using recycled radiation. In particular, the invention relates to such apparatus and methods that employ a radiation source and a +1× system that allows radiation to be recycled through multiple cycles without returning the radiation to the source at an intensity sufficient to interfere with the radiation source's operation.

2. Description of Related Art

The fabrication of integrated circuits (ICs) involves subjecting a semiconductor substrate to numerous processes, such as photoresist coating, photolithographic exposure, photoresist development, etching, polishing, and heating or "thermal processing". In certain applications, thermal processing is performed to activate dopants implanted into functional regions (e.g., source and drain regions) of the substrate and to modify defects in the crystalline lattice of the substrate. Thermal processing includes various heating (and cooling) techniques, such as rapid thermal annealing (RTA) and laser thermal processing (LTP). With LTP, a laser or laser diode array is used to perform thermal processing, and the technique is sometimes called "laser processing" or "laser annealing".

Various techniques and systems for laser annealing of semiconductor substrates have been proposed and used in the integrated circuit (IC) fabrication industry. Laser annealing is preferably done in a single cycle that brings the temperature of the material being annealed up to the annealing temperature and then back down to the starting (e.g., ambient) temperature within a millisecond or less. Thermal cycle times shorter than a microsecond are readily obtained using a single pulse of radiation from a pulsed laser uniformly spread over one or more circuits and a step-and-repeat stage to expose each circuit contained on a large substrate. An example system for performing laser annealing with a pulsed laser source is described in U.S. Pat. No. 6,366,308 to Hawryluk et al.

As an alternative, continuous radiation may be used. For example, thermal processing apparatuses that employ a continuous radiation source in the form of laser diodes are described in U.S. Pat. No. 6,531,681 to Markle et al. As another example, U.S. Pat. No. 6,747,245 to Taiwar et al. describes laser annealing apparatuses that employ $CO_2$ lasers that emit continuous rather than pulsed beams. $CO_2$ lasers have found widespread application in metal cutting and welding applications and therefore are readily available with power levels up to 5,000 Watts.

However, known continuous radiation sources are optimally suited only for certain applications and are not easily adapted to carry out other applications. When used in semiconductor annealing applications, for example, known continuous laser diode beam sources are generally unsuited to deal with circuit density and local reflectivity variations across a semiconductor substrate. Such variations tend to lead to uneven heating of source and drain regions. While the variances in heating may sometimes be reduced by directing the beams toward the substrate at the Brewsters' angle, a 30% variation in absorption across a substrate surface may remain even under fairly ideal conditions.

Thermal processing apparatus employing $CO_2$ laser beams may also suffer from such heating variations. Because the 10.6 micrometer wavelength of $CO_2$ laser beams is long in comparison to any the structures likely to be found on a silicon wafer ready for the dopant activation cycle, the reflectivity at Brewsters' angle typically varies from zero to less than 4% across a typical wafer used in the fabrication of logic circuits. However memory circuits often employ metal gates and in that case the reflectivity can vary from zero to as high as 30%.

To reduce heating variations, a number of techniques have been proposed. In certain cases, a thin absorptive coating could be used to reduce reflectivity variations across a wafer. However, once a coating is applied, it may be necessary to remove it after heating. In other words, coatings necessarily add complexity to already complex manufacturing processes. Furthermore, the application and removal of coatings may result in decreasing device yields. Accordingly, there is a need for technologies that reduce variations in reflectivity without applying and stripping optical coatings from the substrate.

Optical recycling systems have also been proposed as a potential solution to the above-described problem. In general, optical recycling systems collect radiation reflected from a workpiece and reimage the collected radiation back on the workpiece. However, laser beams for welding and cutting are generally focused to a single point. For welding, cutting, and like processes, uniformity over an extended area is not an issue. Instead, efficiency is an issue in such processes. Accordingly, cutting and welding recycling systems can employ a simpler −1× optical recycling system. For example, a welding recycling system may employ a −1× reflective element in the form of a spherical mirror arranged so its center of curvature coincides with the focal point of the laser beam.

In contrast, laser annealing systems for semiconductor substrates tend to employ line or other elongate images that simultaneously heat extended areas on the surface of substrates. Such extended areas may include regions of both high and low reflectance. Accordingly, it is essential that any optical recycling system used for laser annealing apparatus return the reflected radiation back to its point of origin on the substrate and not merely back to another point on the beam image. In other words, the recycling system for such laser annealing systems must collect and reimage radiation from the substrate in a +1× manner. Exemplary +1× systems are described, e.g., in U.S. Pat. No. 7,154,066 to Talwar et al., U.S. Patent Application Publication No. 20050045604 to Talwar et al., and U.S. Patent Application Publication No. 20050189329 to Talwar et al.

Nevertheless, additional opportunities exist to improve recycling systems for laser annealing applications. Such improvement involves overcoming a number of technological challenges via novel and non-obvious ways as described herein.

SUMMARY OF THE INVENTION

In a first embodiment, the invention provides an apparatus for processing a surface of a substrate using recycled radiation. The apparatus includes a radiation source, e.g., $CO_2$ laser, laser diode, etc., positioned to direct a radiation beam toward the substrate surface at a non-normal incident angle to form an image thereon; and a recycling system. The recycling system has an image field that encompasses the beam image on the substrate surface and a conjugate image plane onto which the image may be projected. A reflective element is located in the conjugate image plane. A means is provided for ensuring that radiation from the image field received by the reflective element is directed back toward the image field in a +1× manner. As a result, radiation incident on and reflected from the substrate is recycled through multiple cycles without returning to the radiation source, at an intensity sufficient to interfere with the radiation source's operation.

A number of different recycling systems may be used. Exemplary recycling systems suitable for use with the invention include Offner, Wynne-Dyson, Hershel-Wynne-Dyson, and Dyson systems. When an Offner system is used, a primary mirror, a secondary mirror and at least one reflective element in the conjugate focal plane may be provided. Though different arrangements of optical elements may be possible, the conjugate image plane is typically located closer to the primary mirror than the image field.

The reflective element may include a grating arranged to ensure that radiation reflected thereby does not return to the radiation source after a second reflection from the substrate. The construction of the grating may vary. For example, the image field and the grating may be located within a ring field of an Offner system centered about a ring field axis. The grating may have grating lines that point toward the ring field axis. For example, the grating may be a radial grating that is rotatable about a central grating axis. In addition or in the alternative, the grating may have parallel grating lines, and may have a groove profile that approximates a series of flat steps, and may be laterally translated in a direction approximately normal to the grating lines. In any case, the grating may interact with an incident beam to form a reflected beam so the chief rays in the incident and reflected beams define an NA-measurement plane and the grating may have a blaze angle, the absolute value of which is equal to or larger than the arcsine of the numerical aperture of the beam incident on the grating measured in the NA-measurement plane. This condition assures that the recycled beam after a second reflection from the substrate will not return to the light source.

When a Dyson or Dyson variant recycling system, e.g., Wynne-Dyson or Hershel-Wynne-Dyson, is used, the recycling system may include small air gaps above the object and image planes and a window above the object plane. When the reflective element includes a grating, the window and the grating may be contained in a single movable piece. In any case, the apparatus may further include an aspherized primary mirror of the Dyson recycling system and/or a means for cooling the grating.

In another embodiment, the invention provides an apparatus as described above wherein the recycling system has an image field containing the beam image on the substrate surface referred to as the object plane, which is imaged on an image plane from which it is efficiently reflected back toward the image field in a +1× manner effective to recycle radiation reflected from the substrate through multiple cycles with a radiation loss of about 1% per cycle and without returning the recycled radiation back to the source at an intensity sufficient to interfere with the radiation source's operation. For example, the radiation directing means may be effective to recycle radiation incident on and reflected from the substrate through three cycles.

In another embodiment, the invention provides an illuminator relay in a Dyson system arrangement. The relay includes first, second, and third lens elements that may be nearly identical. The lens elements may not be arranged along a common optical axis as is usually the case, rather than are arranged side-by-side so the plane surfaces of each lens element are approximately in the same plane. The third lens element of the relay may also serve as the refractive element of the Dyson relay. Each lens element has a convex spherical and a plane surface, and each convex surface has a center of curvature located approximately on the plane surface. The relay also includes an object plane parallel to the plane surface of the third lens element and a cylindrical reflective element. The illuminator relay images a uniformly illuminated field located on the center on the plane surface of the first lens element to a distorted intermediate image on the reflective plane surface of the second lens element and then to a uniformly illuminated image on the plane surface, or just below the plane surface of the third or Dyson relay lens.

The relay may be used in combination with a radiation source positioned to direct a radiation beam toward the substrate surface at a non-normal incident angle to form an elongate image on the substrate. In such usage, the elongate image may define a lengthwise axis, the lens elements may be arranged along the lengthwise axis, and the cylindrical reflective element has an axis that is parallel to a line connecting the centers of curvature for the first, second and third lens elements.

BRIEF DESCRIPTION OF THE DRAWINGS

FIG. 6 is a cross-sectional view example embodiment of an Offner optical relay, which illustrates the paths taken by the incident beam, the first recycled beam, the second recycled beam and so on.

FIG. 8A depicts the grating in its entirety in top and cross-sectional views. FIG. 8B shows in a highly magnified schematic a cross-sectional view of a blazed portion of the radial grating blazed so a high proportion of the incident energy is directed into one of the first diffraction orders.

Figure 1:
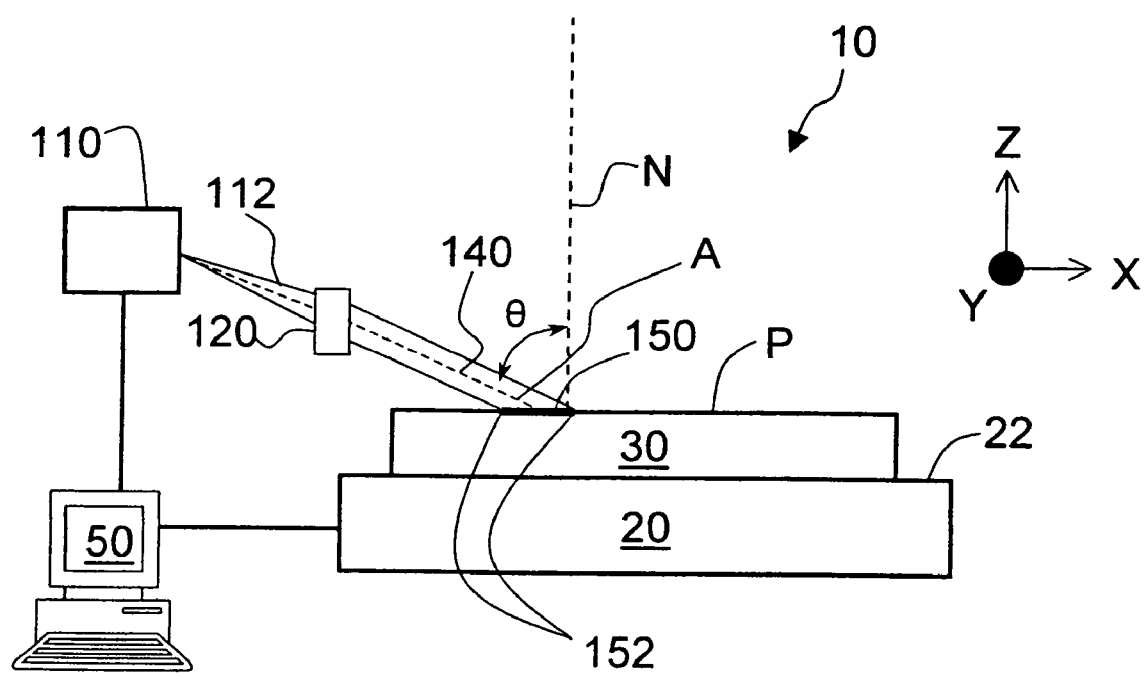
FIG. 1 shows in schematic side view of an exemplary laser annealing apparatus that may be used with a radiation recycling system.

The various elements depicted in the drawings are merely representational and are not necessarily drawn to scale. Certain proportions thereof may be exaggerated, while others may be minimized. The drawings are intended to illustrate various implementations of the invention, which can be understood and appropriately carried out by those of ordinary skill in the art.

DETAILED DESCRIPTION OF THE INVENTION

Definitions

Before describing the present invention in detail, it is to be understood that this invention, unless otherwise noted, is not limited to specific substrates, lasers, or materials, all of which may vary. It is also to be understood that the terminology used herein is for the purpose of describing particular embodiments only, and is not intended to be limiting.

It must be noted that, as used in this specification and the appended claims, the singular forms "a", "an" and "the" include both singular and plural referents unless the context clearly dictates otherwise. Thus, for example, reference to "a beam" includes a plurality of beams as well as a single beam, reference to "a circuit feature" includes a single circuit feature and a set of circuit features, "a layer" includes one or more layers, and the like.

In describing and claiming the present invention, the following terminology will be used in accordance with the following definitions.

The terms "Brewster's angle" or "Brewster angle" is used to refer to the angle of incidence between a radiation beam and a surface normal that corresponds to the minimum or near-minimum reflectivity of the P-polarized component of the beam. Films on the surface of an object, such as a silicon wafer, may prevent it from exhibiting zero reflectivity at any angle. If, however, the films are dielectric in nature, then there generally will be an angle of minimum reflectivity for P-polarized radiation. Accordingly, the Brewster's angle as used herein for a specular surface formed from a variety of different films stacked on a substrate can be thought of as having an effective Brewster's angle, or the angle at which the reflectivity of P-polarized radiation is at a minimum. This angle of minimum reflectivity typically coincides with or is near the angle of the Brewster's angle for the substrate material.

The term "Dyson system" is used in its ordinary sense in an optics context and refers to an optical relay system in which a plano-convex refractive tens element is used in conjunction with a nearly concentric concave reflective element. Unless the context of its usage clearly indicates otherwise, the term "Dyson system" includes Wynne-Dyson, Hershel-Wynne-Dyson, and other variants.

As a related matter, the term "Offner system" is also used in its ordinary sense in an optics context and refers to an all-reflective optical relay system in which a concave primary mirror is used in conjunction with a nearly concentric, convex secondary mirror having a radius of curvature about half that of the primary.

The term "include" and its variants, e.g., "including", are synonymously used with the term "comprise" and its variants, e.g., "comprising" and "comprised of", unless the context of their usage clearly contraindicates such usage.

The term "laser" is used herein in its ordinary sense and refers to a device that emits electromagnetic radiation (light) through a process called stimulated emission. Such radiation is usually, but not necessarily, spatially coherent. Lasers typically, but not necessarily, emit electromagnetic radiation with a narrow wavelength spectrum ("monochromatic" light). The term laser is to be interpreted broadly unless its usage clearly indicates otherwise, and the interpretation may encompass, for example, gas lasers, e.g., $CO_2$ lasers, solid state lasers, and laser diodes and laser diode arrays.

The terms "optional" and "optionally" are used in their ordinary sense and mean that the subsequently described circumstance may or may not occur, thus the description includes instances when the circumstance occurs and instances when it does not.

The term "parallel" is used to describe surfaces that are always the same distance from each other. Thus, surfaces that never meet however far they are extended are considered parallel to each other as well as surfaces that coincide with each other at all points.

The term "semiconductor" is used to refer to any of various solid substances having electrical conductivity greater than insulators but less than good conductors, and that may be used as a base material for computer chips and other electronic devices. Semiconductors may be comprised substantially of a single element, e.g., silicon or germanium, or may be comprised of compounds such as silicon carbide, aluminum phosphide, gallium arsenide, and indium antimonide. Unless otherwise noted, the term "semiconductor" includes any one or a combination of elemental and compound semiconductors, as well as strained semiconductors, e.g., semiconductors under tension and/or compression. Exemplary indirect bandgap semiconductors suitable for use with the invention include Si, Ge, and SiC. Direct bandgap semiconductors suitable for use with the invention include, for example, GaAs, GaN, and InP.

The terms "substantial" and "substantially" are used in their ordinary sense and refer to matters that are considerable in importance, value, degree, amount, extent or the like.

The term "substrate" as used herein refers to any material having a surface, which is intended for processing. The substrate may be constructed in any of a number of forms, for example, such as a semiconductor wafer containing an array of chips, etc.

OVERVIEW OF THE INVENTION

In general, the invention provides apparatuses and methods for processing substrates using recycled radiation, e.g., to anneal semiconductors after ion implantation. The apparatus and methods generally employ a radiation source such as a $CO_2$ laser to direct a radiation beam toward a surface of the substrate at a non-normal incident angle to form an image thereon in conjunction with a +1× optical recycling system that recycles radiation incident on and reflected from the substrate through multiple cycles.

For example, Offner and/or Dyson relay systems may be used that capture the specular reflected component of a radiation beam obliquely incident on a substrate and image or recycle this radiation back to its point of origin on the substrate. This can be done multiple times where required. Recycling can substantially reduce the laser power requirements where the substrate surface is highly reflective and it can significantly improve the temperature uniformity achieved when processing substrates that have a non-uniform surface reflectivity. The recycled radiation can be made to occupy a different angular space than the initially incident radiation beam so interference with the laser source, caused by radiation reflected from the substrate and returned to the source, is minimized without regard to beam polarization. This permits the beam incident on the substrate to be linearly polarized, for example, which is an important consideration for minimizing the initial substrate reflectivity.

The invention is useful for achieving efficient absorption of radiation by the substrate over an extended area that is proportional to the initially incident radiation distribution, e.g., to ensure uniform and efficient substrate annealing. The radiation source may direct a pulsed or continuous radiation beam toward the substrate. The substrate may partially reflective and may even be patterned so the reflectivity varies from point to point over the substrate surface. Depending on the nature of the pattern on the surface, the surface profile, and the wavelength of the incident radiation, the reflected radiation, i.e. the radiation that is not absorbed, may be specularly reflected (as if from a mirror surface) or it may be diffracted or scattered through a wide range of angles. (As used herein, the term "reflected radiation" refers to the radiation component that is not absorbed after a beam is incident on a surface and which therefore includes, for example, specularly reflected radiation, diffracted radiation and scattered radiation.)

For semiconductor annealing applications, it is generally desirable to choose an incidence angle and polarization state for the initial incident radiation beam that maximizes absorption in the substrate. As discussed above, however, the reflected radiation may represent as much as 30% of the initial incident power, depending on the particulars of substrate and the incident wavelength. Even worse, for many applications the variation in the reflected radiation component can vary from zero to 30% from point-to-point across the substrate surface. If no action is taken to recycle this reflected radiation then the reflected radiation is lost and additional power is required in the incident beam achieve a given effect. The variation in reflectivity has an adverse effect on the uniformity of the process.

Radiation recycling may be an important aspect of processes for pulsed thermal annealing semiconductor substrates to activate dopant species implanted into the junction regions. In such thermal annealing applications, a short, intense burst of radiation from a flash lamp or a laser may be used to irradiate a portion of a wafer containing one or more circuits or chips to take the surface temperature from a low temperature (room temperature to 400° C.) to a high temperature (1200° C.-1410° C.). The burst duration in this case might be as long as a few milliseconds or as short as a few tens of nanoseconds. During the burst duration, very little diffusion of heat occurs into the thickness of the wafer. As a result, the bulk of the wafer serves as a heat sink, which cools the surface almost as fast as it was heated. Such a short thermal pulse inhibits any diffusion of the dopants during the thermal cycle, while also promoting a high level of dopant activation. Thus the result is an abrupt junction having low resistivity. Because it is generally impractical to make a radiation source, such as a laser, powerful enough to process an entire wafer with a single pulse, it is necessary to process only a small area at a time and to move the wafer in a step-and-repeat fashion under the radiation beam to obtain full wafer coverage.

An alternate approach is to employ a continuous radiation source formed into a narrow line image on the substrate. The line image can be raster scanned across the wafer to produce a short pulse of radiation on any point on the wafer. In this case the width of the wafer divided by the length of the line image determines the number of scans required and the width of the line image divided by the scan speed determines the pulse duration. With readily available continuous radiation sources and scanning systems it is quite feasible to produce a localized radiation pulse ranging from several milliseconds to a tenth of a millisecond.

Regardless of the thermal processing system used, the size of the instantaneously illuminated field greatly exceeds the thermal diffusion distance. Typical field sizes might span a centimeter or more and the thermal diffusion distance for a millisecond pulse in silicon is the order of 100 micrometers. Thus thermal diffusion cannot be counted on to achieve a uniform temperature distribution over the instantaneously illuminated field. Typical requirements for temperature uniformity are the order of about ±10° C. in a junction annealing application. Assuming the annealing system produces a temperature rise of about 1000° C. then the uniformity of the absorbed radiation has to be about ±1%. If the substrate is patterned and the pattern has a reflectivity variation greater than that required to keep the annealing temperature within acceptable bounds, then recycling the reflected radiation becomes an important and practical means of temperature control.

As discussed above, once the extent of the illuminated area exceeds or approaches the thermal diffusion distance, the magnification of the recycling system must be +1×. Another advantage of employing a +1× system is that alignment between the axis of the recycling system and the illuminated area is not critical. It is the nature of a +1× system to put its image in the same place irrespective of the relay's position, assuming of course it is positioned well enough to gather the light. This is not the case for a −1× relay.

As a related matter, recycling systems having a conjugate image plane represents an improvement in the art because the magnification of the relay from the object to the conjugate image plane is of no consequence. For example, a −5× magnification from the object plane to the conjugate image plane would result in a −1/5× magnification from the conjugate image plane back to the object plane so the net magnification of the returned image would be (−5)(−1/5)=+1×. However −1× relays of the Offner or Dyson variety appear to yield simpler solutions for extended field sizes. Without understanding the requirements underlying the need for a +1× magnification recycling system, those of ordinary skill in the art would not naturally think to design or implement a recycling system that involves the additional complexity of a conjugate image plane.

Another aspect of the invention has to do with the interactions between the substrate and the incident radiation beam. In the case of a wafer containing integrated circuit patterns the patterned film geometries and film thicknesses tend to be less than a micrometer in extent. This is very much smaller than the 10.6 micrometer wavelength of a $CO_2$ laser so an incident $CO_2$ laser beam, tends to be either absorbed or specularly reflected and very little of the incident radiation is scattered or diffracted. If the laser beam is incident the substrate at a high incidence angle then scattering and diffraction are even further suppressed. This is in sharp contrast to what happens if a laser diode beam with a wavelength of 0.8 micrometers is employed. In this case the beam wavelength and the pattern size and film thicknesses are comparable and the scattering and diffraction components are relatively high. Thus, a high NA relay, such as a Dyson relay, might be required for short wavelengths that tend to scatter and diffract through large angles and a lower NA relay, such as an Offner system, might be employed with a longer wavelength annealing system.

Still another aspect of the invention has to do with the interaction between the recycled beam and the laser source.

Laser based systems employing a beam focussed to a point and normally incident on a substrate surface generally employ a quarter wave plate and a polarization sensitive beam splitter to keep the reflected beam from re-entering the laser cavity where it can cause serious instability problems and even result in damage to the cavity mirrors. With this arrangement the linearly polarized output beam from the laser is transmitted through the polarization sensitive beam splitter and is converted to circularly polarized light after passage through the quarter wave plate. After reflection from the substrate the circularly polarized radiation passes again through the quarter wave plate and is converted into linearly polarized light oriented orthogonal to the original polarization so it is reflected by the beam splitter and does not make its way back to the laser cavity. Unfortunately this scheme doesn't work if it is desired to have a linearly polarized beam incident on the substrate to minimize the substrate reflectivity or the reflectivity variation.

If polarized radiation incident at a large angle, such as the Brewsters' angle, is employed to minimize the reflected radiation component then the reflected radiation is directed away from the incident beam direction and is generally not a problem. However if the reflected beam is recycled, then it is quite possible that the recycled beam, if reflected from the substrate a second time, will re-enter the laser cavity causing problems. The possibility of a recycled beam re-entering the laser cavity needs to be seriously considered in the design of a recycling system. If it is desired to employ linearly polarized radiation on the substrate and to recycle the specularly reflected light from the substrate then interaction between the recycled light and the radiation source can be avoided if the radiation beam is incident the substrate at non-normal incidence and if the recycled light is incident the substrate so it specularly reflects at angles outside of the angular space occupied by the incident light from the radiation source. A possible exception might be a beam that has been recycled so many times that it has negligible intensity. Using different angular spaces for the incident and recycled beams almost inevitably leads to recycling relays that are capable of operating at very high numerical apertures in at least one direction. The Dyson system is known to operate at a high NA while the Offner system is generally limited to NAs below 0.2, however it turns out the Offner system is capable of operating at a much higher NA in one direction and therefore it is useful as a recycling relay system.

Exemplary Annealing Apparatus for Use with Recycling System

In the following description of the embodiments of the invention, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that changes may be made without departing from the scope of the present invention. The following detailed description is, therefore, not to be taken in a limiting sense, and the scope of the present invention is defined only by the appended claims.

To illustrate the novel and non-obvious aspects of the invention, FIG. 1 schematically depicts a thermal processing apparatus 10 that may be used to anneal and/or otherwise thermally process one or more selected surface regions of a substrate according to the present invention. LTP system 10 includes a movable substrate stage 20 having an upper surface 22 that supports a semiconductor substrate 30 having an upper surface P and a surface normal, N, thereto. Substrate stage 20 is operably coupled to controller 50. Substrate stage 20 is adapted to move in the X-Y plane under the operation of controller 50 so the substrate can be scanned relative to the beam image generated from radiation provided by radiation source 110. Stage 20 may also controllably rotate substrate 30 about a Z axis which extends orthogonally relative to the X-Y plane. As a result, the stage 20 may controllably fix or alter the orientation of substrate 30 in the X-Y plane.

The stage may include different components to carry out different functions. For example, an alignment system may be provided to position the substrate on the stage at a variable orientation angle relative to X and Y-axis and about the surface normal. In such a case, the stage may independently control the substrate movement while the alignment system controls the substrate orientation.

The radiation source 110 is operably coupled to controller 50, and a primary relay 120 that serves to relay radiation generated by the radiation source toward the substrate to form a beam image on its surface. In an exemplary embodiment, radiation source 110 is a $CO_2$ laser that emits radiation at a wavelength $\lambda_H$~10.6 μm (heating wavelength) in the form of beam 112. However, the radiation suitable for use with the invention may include LED or laser diode radiation as well, e.g., radiation having a wavelength of about 0.8 μm. Optionally, a plurality of radiation sources may be employed. As shown, the laser 110 generates an input beam 112 that is received by a primary relay 120 that is adapted to convert the input beam to an output beam 140 that forms a beam image 150 on the substrate.

Optionally, the intensity profile of the beam is manipulated so a portion of the image intensity is rendered uniform about its peak intensity for even heating and high energy utilization. For example, the primary relay 120 may transform the input beam 112 into output beam 140. The primary relay may be constructed in a manner to provide for desired coherent beam shaping so the output beam exhibits a uniform intensity profile over a substantial portion thereof. In short, the primary relay 120 and the radiation source 110 in combination may stabilize, the directionality, intensity profile, and phase profile of the output beam to produce a consistently reliable laser annealing system.

Beam 140 travels along optical axis A, which makes an angle θ with a substrate surface normal N. Typically, it is not desirable to image a laser beam on a substrate at normal incidence because any reflected light may cause instabilities when it returns to the laser cavity unless polarizers and quarter wave plates are used to exclude reflected light. Another reason for providing optical axis A at an incidence angle θ other than at normal incidence is that efficiently coupling of beam 140 into the substrate 30 may best be accomplished by judicious choice of incidence angle and polarization direction, e.g., making the incidence angle equal to the Brewster's angle for the substrate and using p-polarized radiation. In any case, the stage may be adapted to scan the substrate through the beam position while preserving the incidence angle. Similarly, the stage may be adapted to control, fix or vary the orientation angle of the substrate relative to the beam axis.

Beam 140 forms beam image 150 at substrate surface P. In an exemplary embodiment, beam image 150 is an elongate image, such as a line image, having its lengthwise boundaries indicated at 152, and located within a plane containing the incident beam axis and the surface normal (N). Lengthwise boundaries for images having a set fraction of a substantially Guassian intensity profile may represent the useful portion of the image for thermal processing. Accordingly, the incidence angle of the beam (θ) relative to the substrate surface normal N may be measured in this plane. Surface incident angle θ may be, for example, the (effective) Brewster angle for the substrate.

Controller 50 may be programmed to provide relative movement between the stage and the beam. Depending on the desired process parameters, the controller may provide different types of relative movement. As a result, the beam image 150 may be scanned along any desired path and at any desired velocity on the substrate surface to heat at least a portion of the substrate surface. Typically, as discussed below, such scanning may be carried out in a manner effective to achieve a desired temperature within a predetermined dwell time effective to transform the microstructure of the circuit layer to exhibit electronic properties suitable for forming circuit features therein. Scanning may typically be performed in a direction that is orthogonal to the lengthwise axis of the image although this is not a firm requirement. Non-orthogonal and non-parallel scanning may be carried out as well.

Reflectivity Variations

In order to recycle radiation reflected from the beam image to achieve uniform heating, variations in the reflectivity of the substrate surface should be taken into account. In particular, it has been observed that silicon wafers with microelectronic devices formed therein tend to have different reflective properties depending on the functionality of the devices. That is logic wafers, e.g., silicon wafers having logic devices formed therein, tend to exhibit different reflective properties than memory wafers, e.g., silicon wafers having memory devices with metal connections formed therein.

Figure 2:
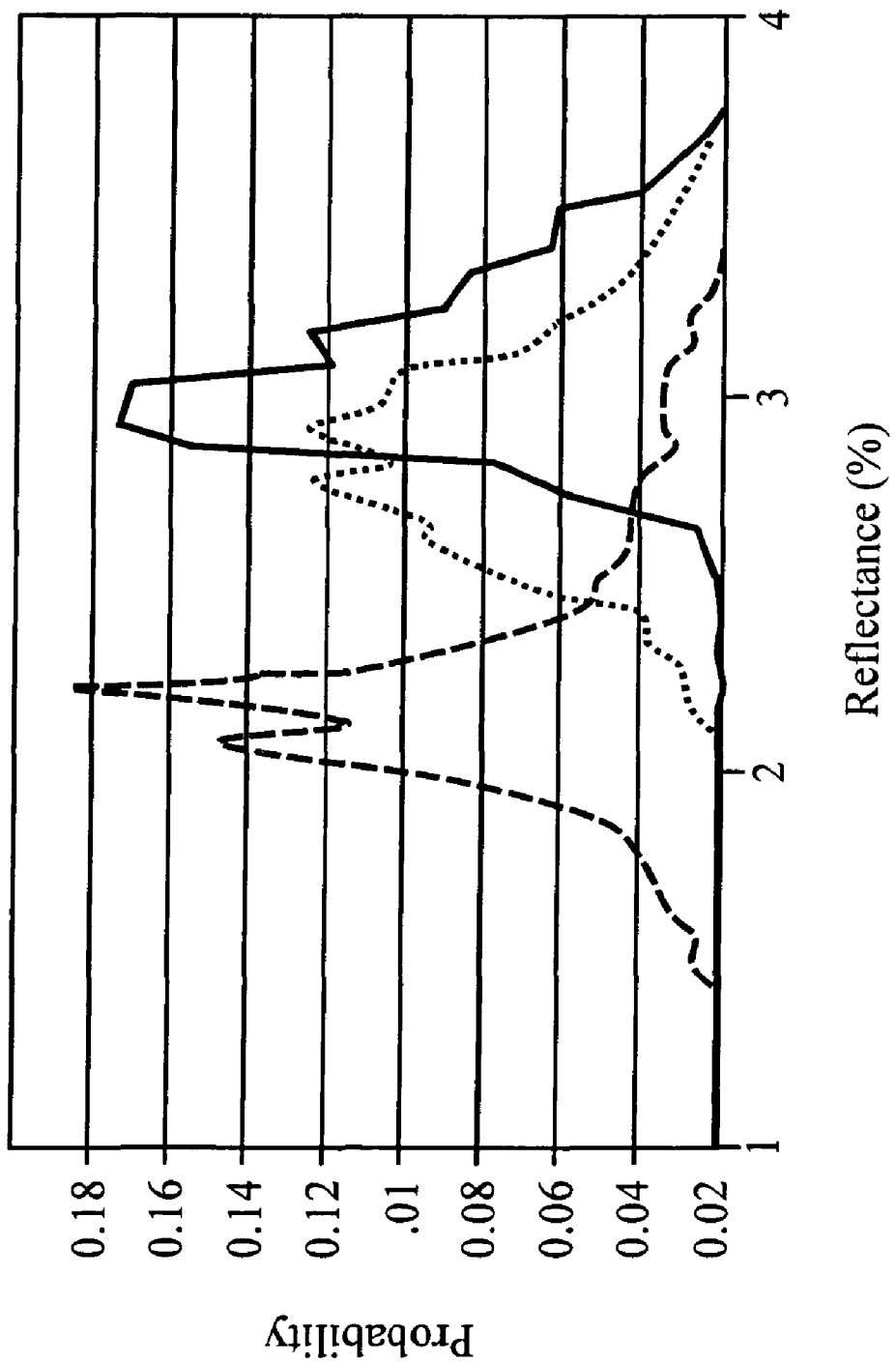
FIG. 2 graphically depicts measured reflectivity distributions obtained from three silicon logic wafers using p-polarized, 10.6 micrometer radiation incident at Brewsters' angle.

For example, FIG. 2 graphically shows the probability of finding a spot with a specific reflectivity on three different logic wafers, which contain patterned dielectric films. The variation in reflectivity for the wafers ranges from about zero to 4%. Assuming that annealing apparatus generally produces an average temperature rise of about 1000° C., the variation in reflectivity for the wafers would lead to a peak annealing temperature variation of about 40° C. This estimate also assumes that the beam size employed to obtain the data in FIG. 2 is about equal to or greater than the thermal diffusion distance, which happens to be the case with these measurements. In this case, a single recycling cycle having 98% efficiency would reduce the effective non-uniformity from 4% to about 0.237% corresponding to a temperature variation of 2.4° C. A temperature variation of 2.4° C. may be adequate for many annealing applications.

Figure 3:
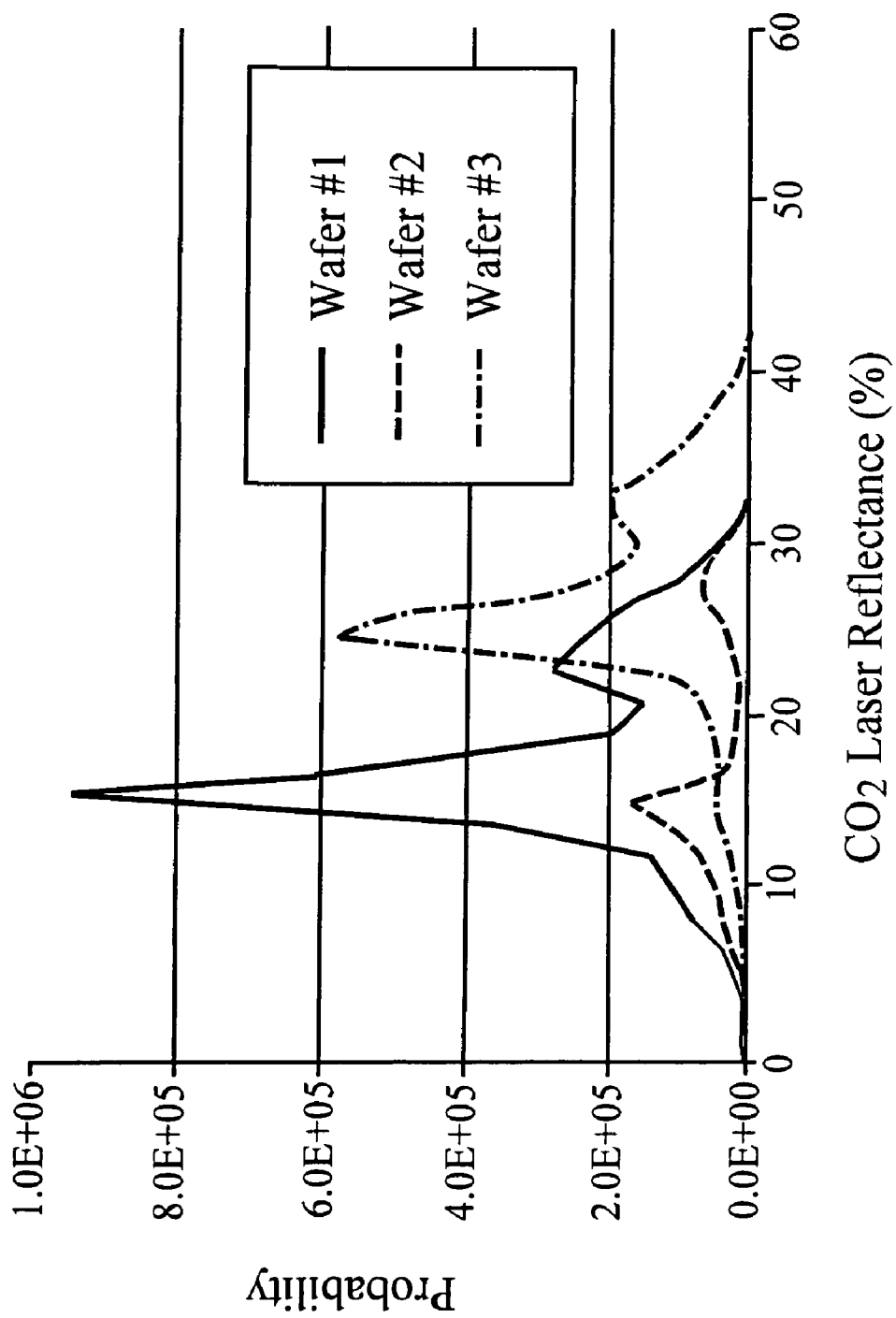
FIG. 3 graphically depicts measured reflectivity distributions obtained from three silicon memory wafers using p-polarized, 10.6 micrometer radiation incident at Brewsters' angle.

FIG. 3 graphically illustrates the probability of finding a spot with a specific reflectivity on three different memory wafers which contain patterned dielectric and metal films. The total variation in reflectivity for the memory wafers is about 40%. Assuming that annealing apparatus generally produce an average temperature rise of about 1000° C., the variation in reflectivity for the wafers would lead to a peak annealing temperature variation of about 400° C. Such a variation would be unacceptable for most annealing applications. In this case, a single recycling cycle having 98% efficiency would reduce the effective non-uniformity to only about 16.5%. However, two recycling cycles would reduce the non-uniformity to 7.3%, 3 recycles to 3.6%, and 4 recycles to 2.2%. Thus for some substrates, e.g., memory chip substrates, multiple recycling cycles are necessary to obtain the uniformity required for annealing applications.

Another important consideration in recycling is the wavelength of the radiation used for annealing relative to the physical dimensions of the patterns on the substrate since this determines the amount of scattering from the substrate. In this context, scattering is the proportion of radiation that is neither absorbed nor specularly reflected from the substrate and it is assumed that all of the light entering the substrate is absorbed (and not transmitted). For example, if light having a wavelength of 10.6 micrometers from a $CO_2$ laser is used to anneal a wafer containing sub-micrometer geometry patterns, then very little radiation is scattered, i.e. less than 1%, and almost all of the incident radiation is either absorbed or specularly reflected. However if 800 nm radiation from a diode array is used for annealing patterns of comparable size, an appreciable proportion of the incident radiation may be scattered. The scattered radiation must be taken into account when estimating the efficiency of the recycling system. In general, the directions and the relative intensities of the scattered radiation will depend on the nature of the pattern and therefore can be expected to vary from point-to-point across each circuit.

Offner Recycling Relay

As discussed above, Offner relays may be used to recycle radiation according to the invention. Originated by Abe Offner, Offner relays may be used to recycle radiation in situations where scattered radiation is minimal, e.g., when a $CO_2$ laser is used to anneal semiconductor wafers. Offner relays have an all-reflective construction, as opposed to relays that use one or more refractive lenses.

Figure 4A:
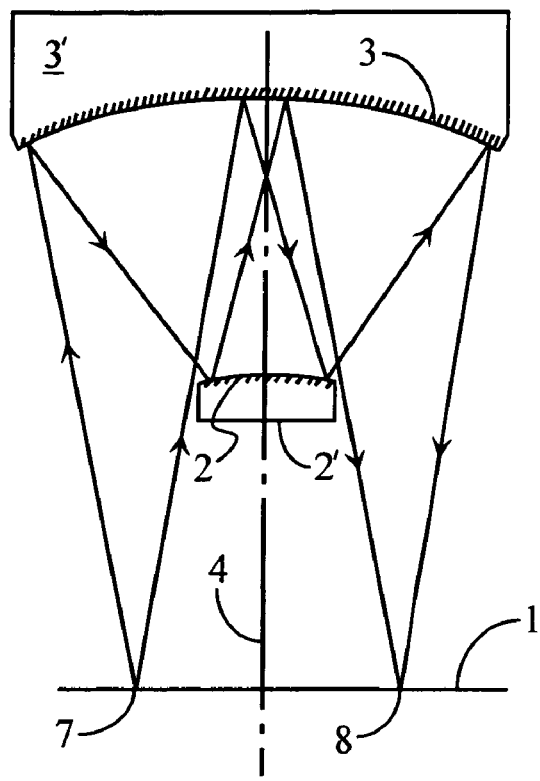
FIGS. 4A and 4B, collectively referred to as FIG. 4, provides a cross-sectional schematic views of an all-reflective Offner relay that can be used to image a narrow laser beam image reflected from a substrate onto a reflective grating and then back to the substrate.
Figure 4B:
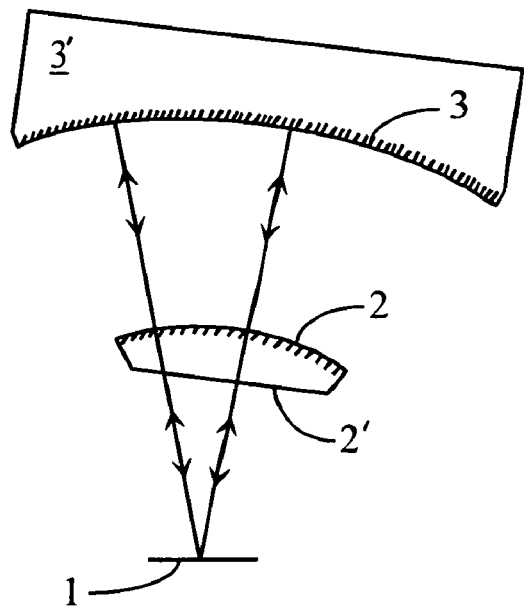

FIG. 4 shows cross-sectional views of an Offner recycling relay of the type suitable for use with the invention. As shown, the Offner recycling relay has a two-mirror, 3-reflection construction. In FIG. 4 surfaces 3 and 2 are spherical reflective surfaces on a primary mirror 3' and secondary mirror 2', respectively. An object point 7 is reflectively imaged onto image point 8 located on the opposite side of the optical axis 4 of the Offner recycling relay (FIG. 4A). The centers of curvature of both mirrors are nearly coincident and located near the object and image planes, which are all located on a common plane 1 (FIG. 4B) with the radius of curvature of each of mirrors 2' and 3' being substantially the same.

Figure 5:
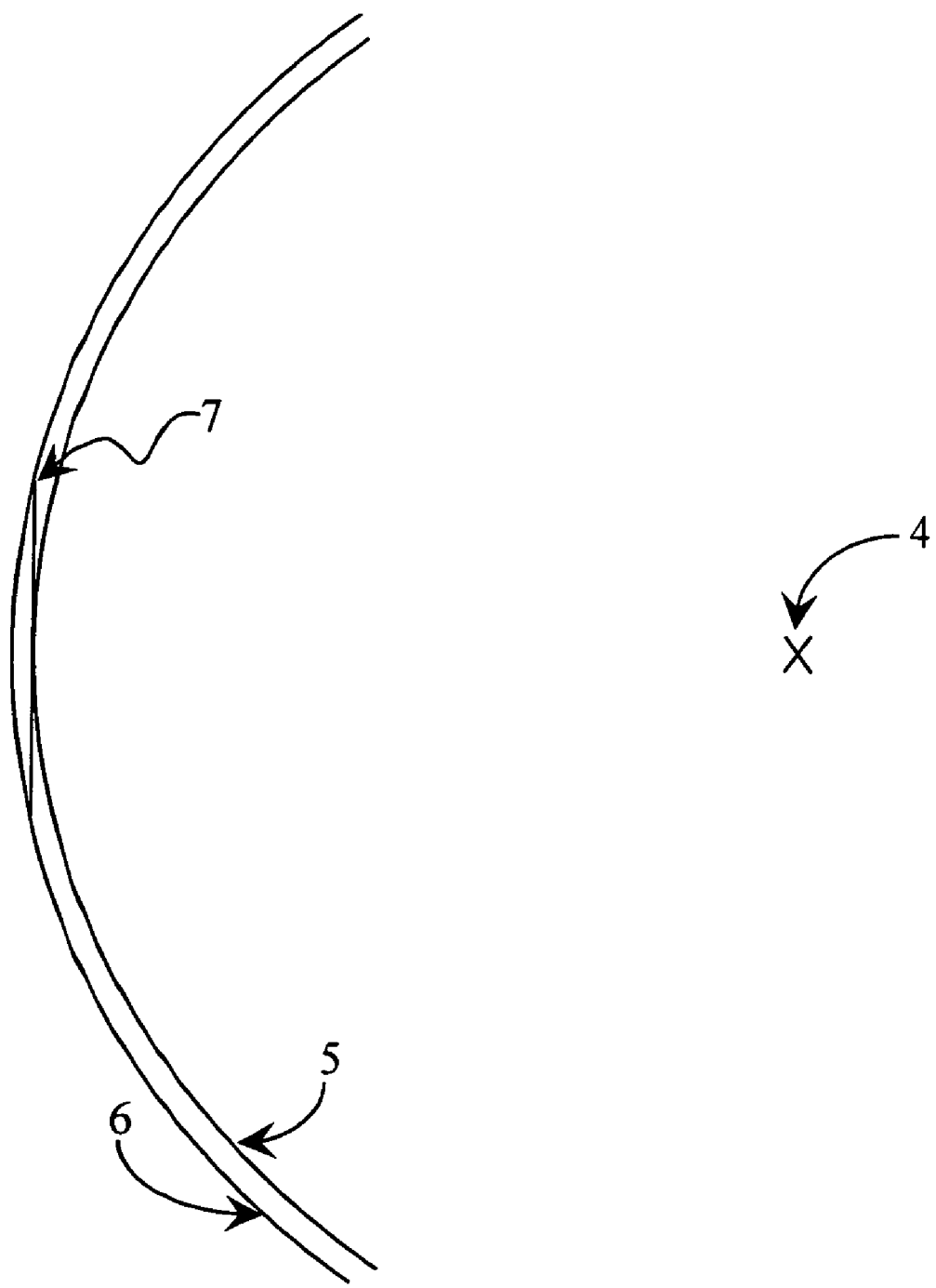
FIG. 5 is a schematic illustrating how a narrow line-image can be contained in a narrow ring-field typical of an Offner relay.

The useful field of the Offner system is a narrow annular ring, bounded by arcs 5 and 6 and concentric with the optical axis 4, as shown in FIG. 5. FIG. 5 also illustrates how a long narrow image 7' can be contained in the annular field of the Offner recycling relay.

An exemplary design specification for an all-reflective Offner recycling relay is shown in Table 1:

TABLE 1

| Surface | Thickness | Radius |
|---|---|---|
| Substrate | 131 mm | |
| Primary Mirror | −63.311 mm | −129.032 mm |
| Secondary Mirror | 63.311 mm | 65.720 mm |
| Primary Mirror | −127.065 mm | −129.032 mm |
| Grating | | |

Ring field radius is 26.35 ± 0.917 mm and NA is 0.18

An interesting aspect of the Offner recycling relay when used in conjunction with annealing apparatuses described above is that the numerical aperture (NA) is limited to about 0.2 in the plane containing the offset direction, i.e. the plane containing the optical axis and the normal to the middle of the long laser beam image. However in the plane parallel to the laser beam image 150 the NA can be made extremely high. Also it is possible to displace the object and image planes by small equal and opposite amounts along the optical axis 4 without appreciably upsetting the good aberration correction provided by the design. This has been done with the design shown in Table 1.

The magnification of the Offner recycling relay from the object plane 7 to the reflective image plane 8 is nominally −1×. If, however, a mirror or a reflective grating is placed in the reflective image plane 8 to recycle the radiation back to the object plane 7 then the magnification of the double-pass arrangement from the object plane 7 to the image plane 8 and back to the object plane 7 is +1×. A +1× magnification recycling systems allows points in the object plane to be imaged back on themselves perfectly, whereas a −1× magnification would result in an inverted image.

In any case, the Offner recycling relay construction described above is very forgiving of alignment errors. Small lateral displacements of the mirrors or gratings in the reflective image plane 8 have no effect on the position of the +1× image. Similarly, small displacements of the Offner recycling relay or the individual recycling relay components have no effect on the +1× image position, which is always perfectly superimposed on the original image 7'.

Figure 6:
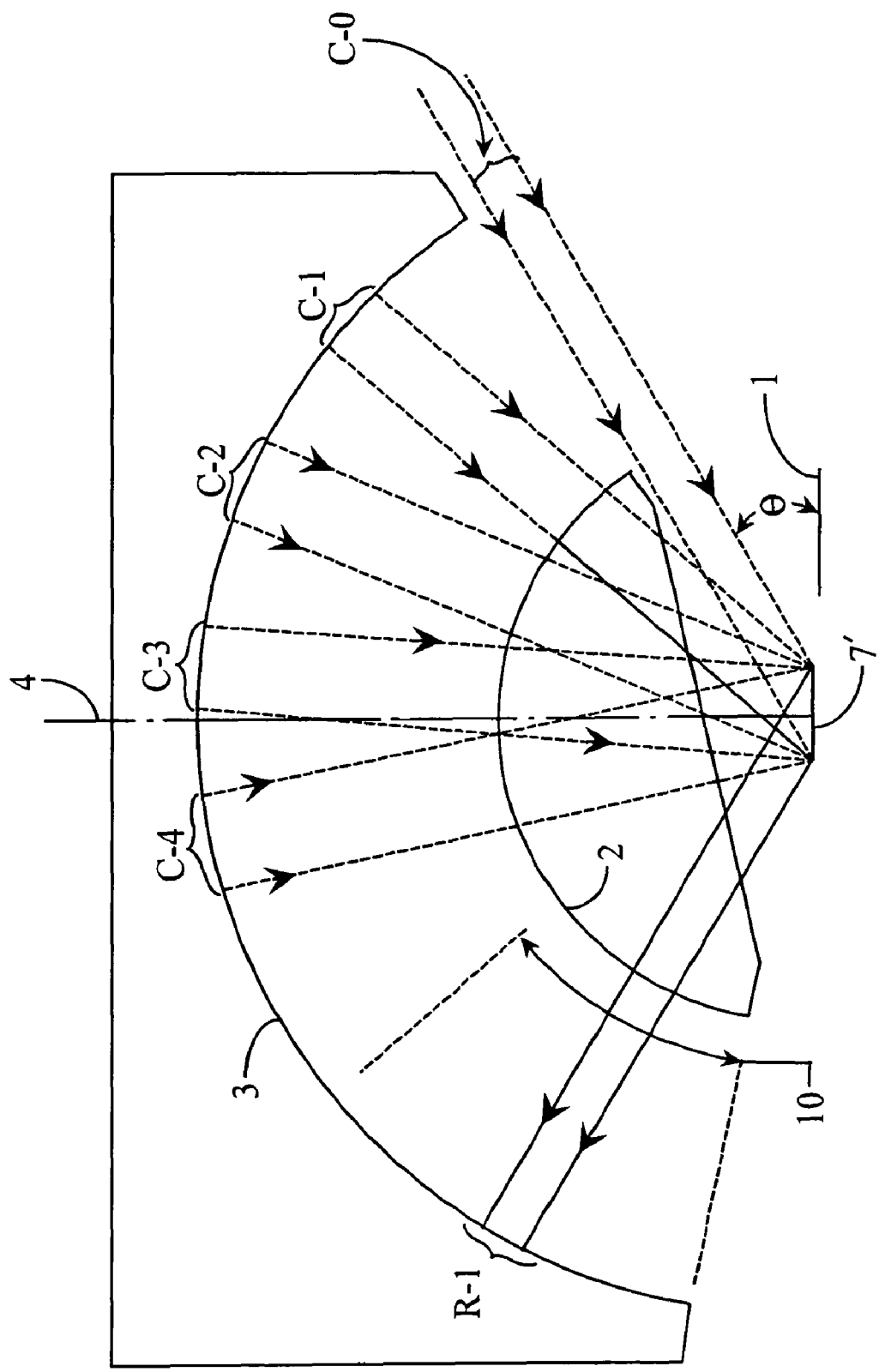

FIG. 6 shows in cross-sectional view how an Offner recycling relay, when employed with annealing apparatuses described herein, can be extended in a direction parallel with the long dimension of the laser beam image 150 (FIG. 1) so multiple reimaging cycles are possible. FIG. 6 is an annotated version of FIG. 4B. In this example, the incident beam, C-0 (140 in FIG. 1), is collimated and is incident on the substrate at an angle φ of 60° corresponding to an angle θ of 30° in FIG. 1 from a normal substrate 30 as laser beam image 7' (150 in FIG. 1). The specularly reflected component of the incident beam, R-1, on surface 3 of primary mirror 3' is reimaged by surface 2 and back to surface 3 to the opposite side of optical axis 4 where it is incident on a grating that is blazed to efficiently diffract or reflect the light into an angle corresponding to the angle taken by beam C-1. Radiation reflected from the grating is then reimaged (recycled) by the recycling relay onto the substrate 1 (30 in FIG. 1) on top of the initial laser beam image 7'.

From FIG. 6, it is clear that the specularly reflected component of recycled beam C-1 will also be reimaged by the recycling relay onto the reflective grating 3 on the beam image 7' side. The diffracted/reflected beam from the gratings 2 and 3 is reflected at an angle corresponding to beam C-2 and after passing through the Offner recycling relay a fourth time is incident on the substrate at 7' at a lower angle of incidence. The reflected component of this beam from the substrate is also recycled (as are beams C-3, C-4, etc) until the recycled beam eventually finds its way out of the recycling system. In short, the invention provides for beam recycling through one, two, three, four, or more cycles.

Figure 7:
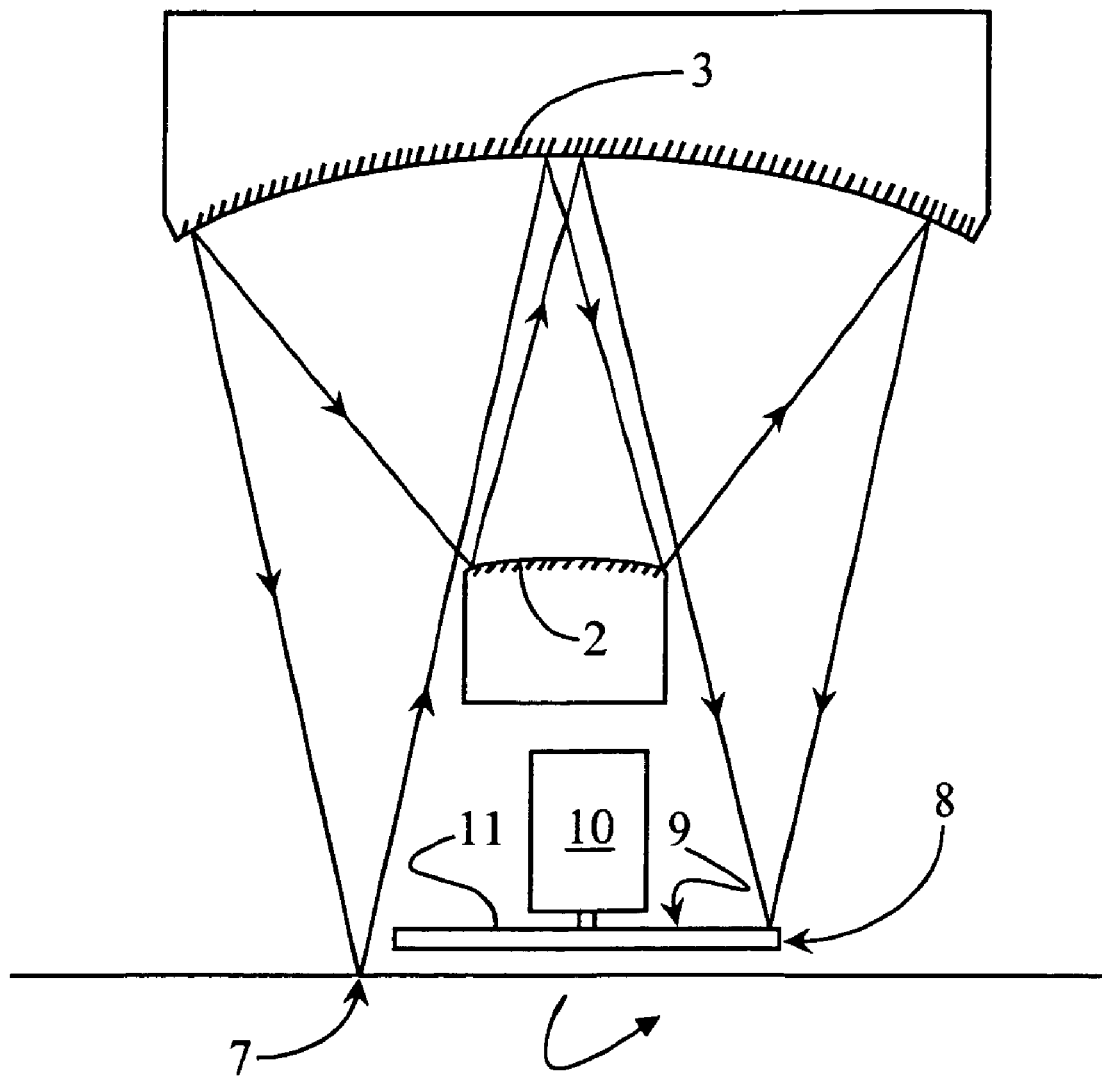
FIG. 7 is a schematic diagram that illustrates how the object and image planes in an Offner relay can be adjusted so the image plane is above the object plane and thereby affords room for a spinning a radial grating.

FIG. 7 depicts a relay similar to that shown in FIG. 4A, illustrates how the object and image planes can be displaced by equal and opposite directions along the optical axis to make room for the reflector or grating at the image plane 8. An object point 7 on the substrate 1 is imaged by the relay to image point 8 on a reflective grating 9. In this case grating 9 consists of a series of radial grooves on a circular substrate 11 that is continuously spun by a motor 10 located close to the optical axis of the relay. Grating 9 is made to be as reflective as possible and would likely be damaged by the very high intensity of the incident laser beam if it were not actively cooled or continuously moved to spread the heat over a much larger area. A second advantage of employing a moving grating is that the motion introduces a frequency shift in the recycled beam that eliminates the standing interference pattern that would result from a fixed grating. The typical $CO_2$ laser is coherent over a path length that is much longer than the round trip through the Offner relay so an interference pattern caused by the interaction between the directly incident laser beam and the recycled beams incident at slightly different angles is to be expected. The change in frequency between the incident beam and the recycled beams causes the interference patterns to move and if the rate of motion is sufficient then the interference effects can be averaged out over the dwell time, i.e. the time taken for the laser beam to pass over a point on the substrate.

Figure 8A:
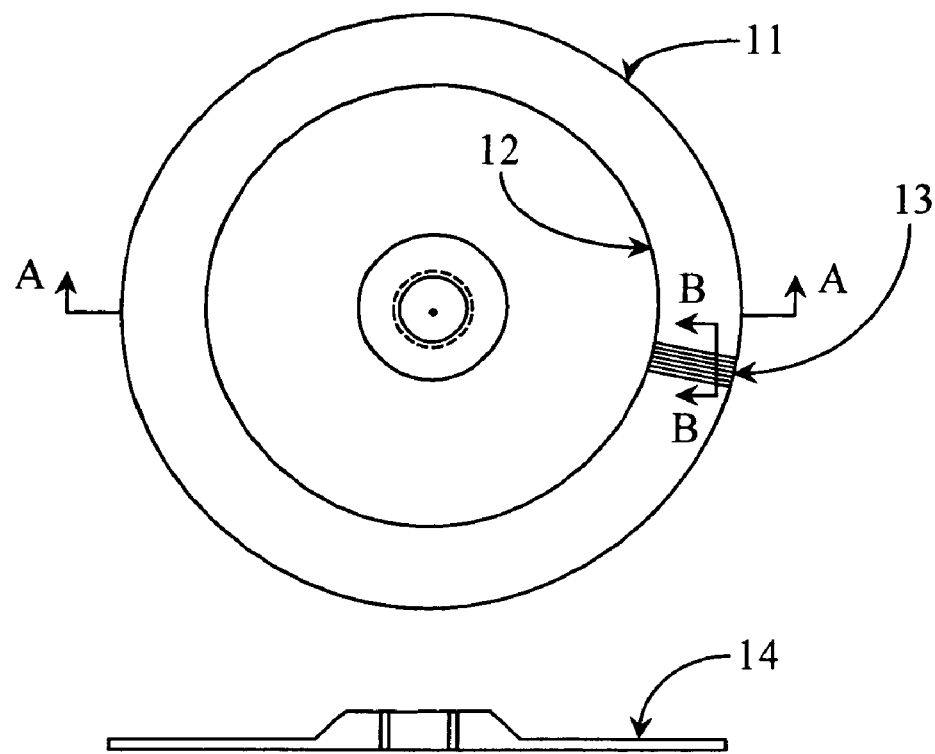
FIGS. 8A and 8B, collectively referred to as FIG. 8, schematically depict a radial grating contained on the outer raised portion of a circular disk, which may be spun about its axis.
Figure 8B:
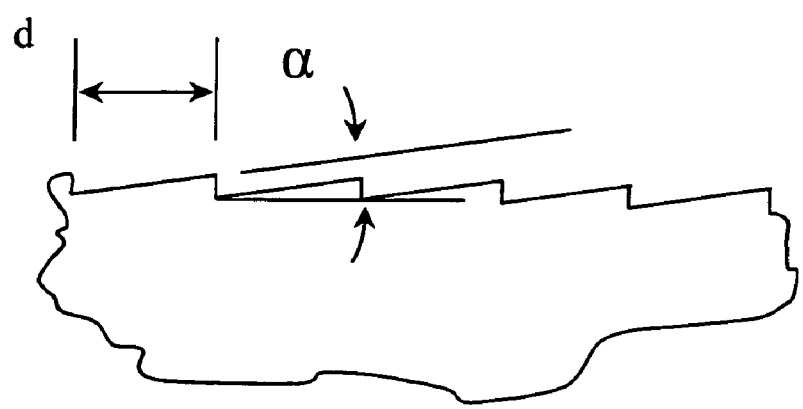

The function of the grating 9 is to redirect the incident light so the recycled light stays locked into the recycling system for as many cycles as possible, while preserving focus. A tilted mirror would suffice to redirect the incident light efficiently however would not preserve the location of the flat focal plane normal to the optical axis. A design schematic for a radial grating is shown in FIG. 8A. In this case, the upper, outer part of the disk contains a raised portion, 14, included between the outer diameter 11 and an inner diameter 12, which contains the radial grating pattern. A magnified section through the blazed grating 9, which consists of a series of shallow flat steps, as shown in FIG. 8B. Each of the step surfaces is inclined at an angle α and serves as a mirror to deflect the reflected or diffracted radiation through a deflection angle of 2α. Ideally the path difference in reflecting from one step to the next is an integral number of wavelengths (λ); however this will depend on the incident and diffracted angles and can be expected to change depending on the recycle number. The relationship for an ideal grating is given by the grating equation:

$$n\lambda = d(\sin\theta_1 - \sin\theta_2) \quad (1)$$

where: n is an integer known as the diffraction order; λ is the wavelength of the radiation; d is the grating spacing; $\theta_1$ is the incidence angle measured from the grating normal; and $\theta_2$ is the diffraction angle measured from the grating normal.

The blaze angle, α, is half of the deflection angle. Thus, for example, when the radiation wavelength is chosen to be 10.6 micrometers, the diffraction order 3, the incidence angle 60°, and the grating spacing 160.65 micrometers, the resulting diffraction angle is 41.919°. Since the deflection angle is the difference between the incidence and diffraction angles, the deflection angle is $\theta_1-\theta_2$, or 18.081°. This yields an optimum blaze angle of 9.04°.

The diffraction angle for the last recycle becomes minus, the incidence angle for the next cycle for the second recycle the diffraction order becomes 4, the diffraction angle becomes 23.838° and the optimum blaze angle is (41.919°−23.838°)/2=9.04°. Thus the same blaze angle is optimum for the first and second recycles.

Since the power in the recycled beam decreases with each recycle the grating efficiency matters less with each additional recycle. For the third recycle, assuming a fifth order diffraction, the diffraction angle becomes 4.2577° and the optimum blaze angle is 9.8°. This angle is close enough to the previously calculated angle of 9.04° that a high efficiency diffraction/reflection is still obtained where it is desired.

Figure 9:
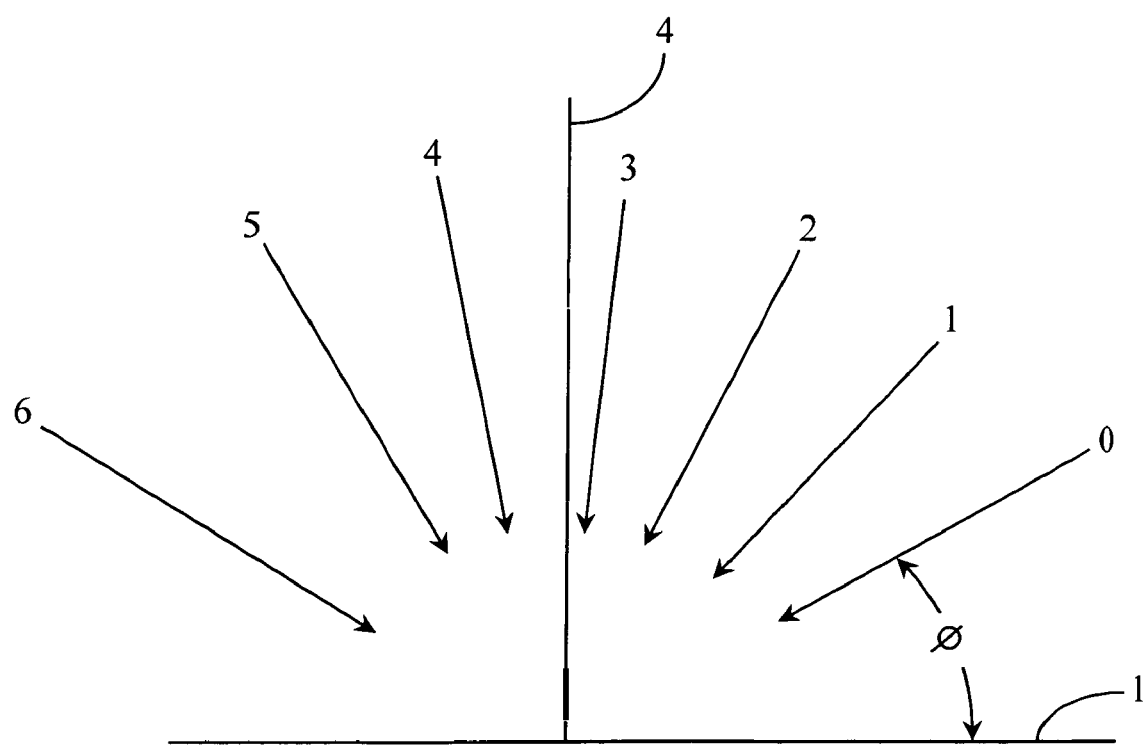
FIG. 9 schematically shows how the incidence angle direction of the chief ray with respect to the substrate normal might be expected to change depending on the number of times it is recycled.

FIG. 9 shows the direction of the chief ray for the incident beam (zero order recycle) and for each successive recycle up to the $6^{th}$. Beyond the $6^{th}$ recycle the beam is lost from the recycling system however the energy in the beam at this point is probably negligible. For example if the substrate exhibits a 40% reflectivity, then the intensity of the beam after the $6^{th}$ recycle is $(0.4)^7=0.1638\%$.

By making the blaze angle sufficiently small it is possible, in theory, to make the number of possible recycles arbitrarily large. However this assumes that the incident beam is perfectly collimated and that the collimation remains intact after reflecting from the patterned substrate multiple times. The schematic shown in FIG. 6 assumes that a collimated beam is incident on the substrate while the reflected beam has an effective NA of 0.18, which must be intercepted by the Offner relay. It also assumes the grating deflects the incident beam sufficiently so it can be separated from the collimated incident beam and this leads to a deflection angle by the grating of about 18°. Different assumptions about the angular spread imparted to the incident beam by the pattern would lead to a different design and a different maximum number of possible recycles.

The radial groove pattern of the grating shown in FIG. 8 allows the grating to be spun about its central axis, which offers several advantages. Spinning spreads the energy absorbed from the incident laser beams over the entire diameter of the grating disk thereby greatly diminishing the maximum temperature reached by any point on the disk and also facilitating cooling of the heated portions of the disk by the motion through the ambient air. At the 10.6 micrometer $CO_2$ laser wavelength the reflectivity of the grating coating can be made to exceed 99% so only a small portion of the incident radiation is absorbed however, depending on the rotational velocity of the grating disk, the dwell time can be longer than that experienced by the substrate since the rotational motion of the disk is in the long direction of the beam image. The spinning disk also introduces a Doppler shift in the wavelength of the reflected radiation that smears out the interference pattern on the substrate that would otherwise be created by the directly incident and the recycled beams. Generally the coherence length of a $CO_2$ laser greatly exceeds the round trip path length from the substrate to the grating and back to the substrate.

An estimate of the rotational speed necessary to completely average out the interference effects can be obtained assuming that in one dwell time period the path length from a fixed point in space above the grating will be changed by 10 wavelengths. Assuming the grating order is 3, the pitch between grooves is 160 micrometers and the dwell time is 1 millisecond, then in 1 millisecond it will be necessary to move the grating 533 micrometers. If the effective grating diameter is 46 mm then the angular rotation rate corresponds to 3.69 revolutions per second or 221 revolutions per minute.

Figure 10:
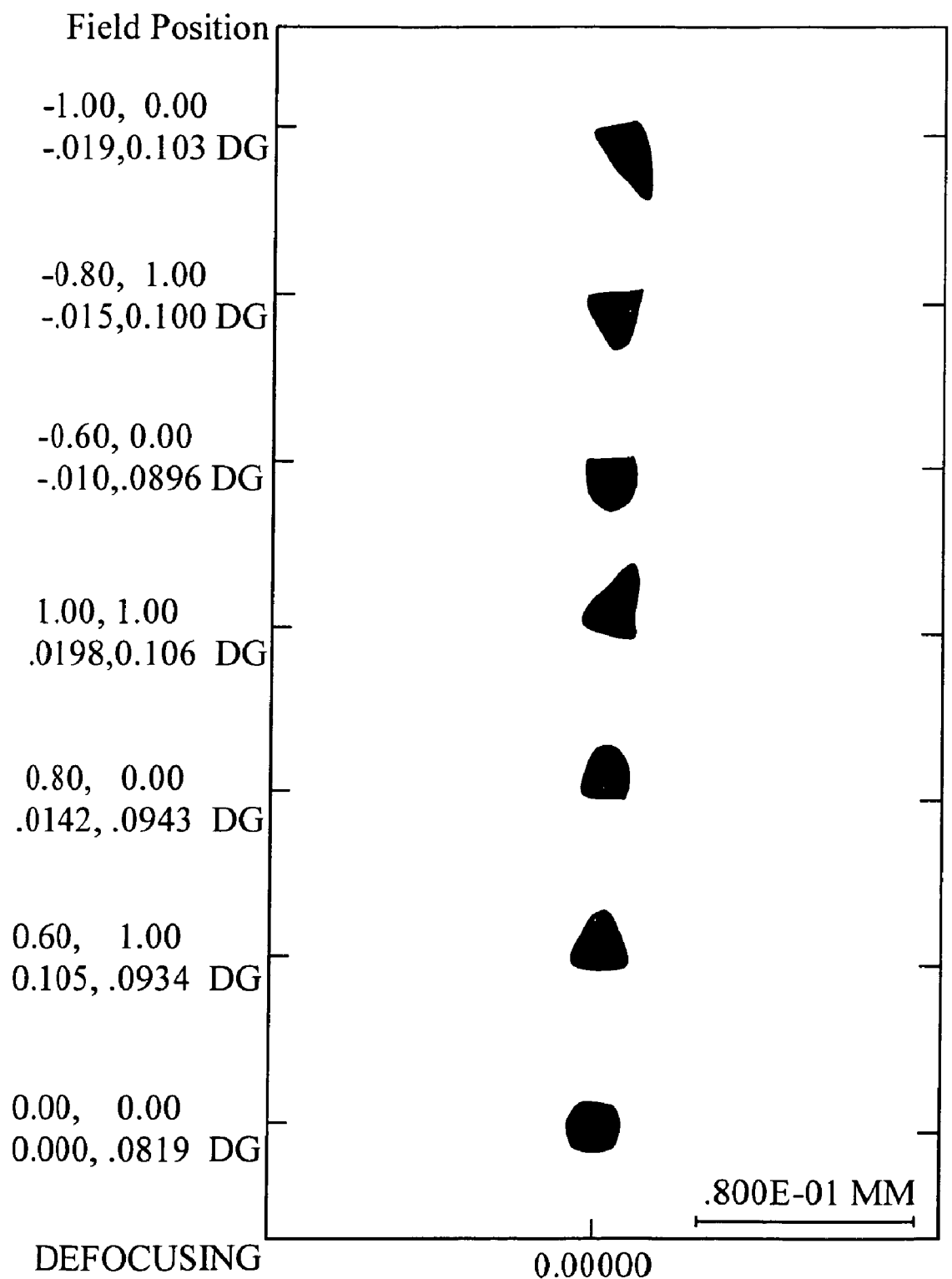
FIG. 10 is a plot showing the blur circle size corresponding to different points in the ring field of the Offner relay.

As another example, one may employ an Offner system similar to that described in Table 1 that has a 0.17 NA in the radial direction, sufficient NA in the tangential direction to span an included angle of about 132°, and a field size of 10 mm by 0.2 mm. The blur circle size after a double pass through this system, shown in FIG. 10, is largest at the field extremities, and does not exceed 50 micrometers. This is about equal to the thermal diffusion distance so the maximum distance for a return ray from its point of origin on the substrate is about half of the thermal diffusion distance.

Dyson System

Figure 11:
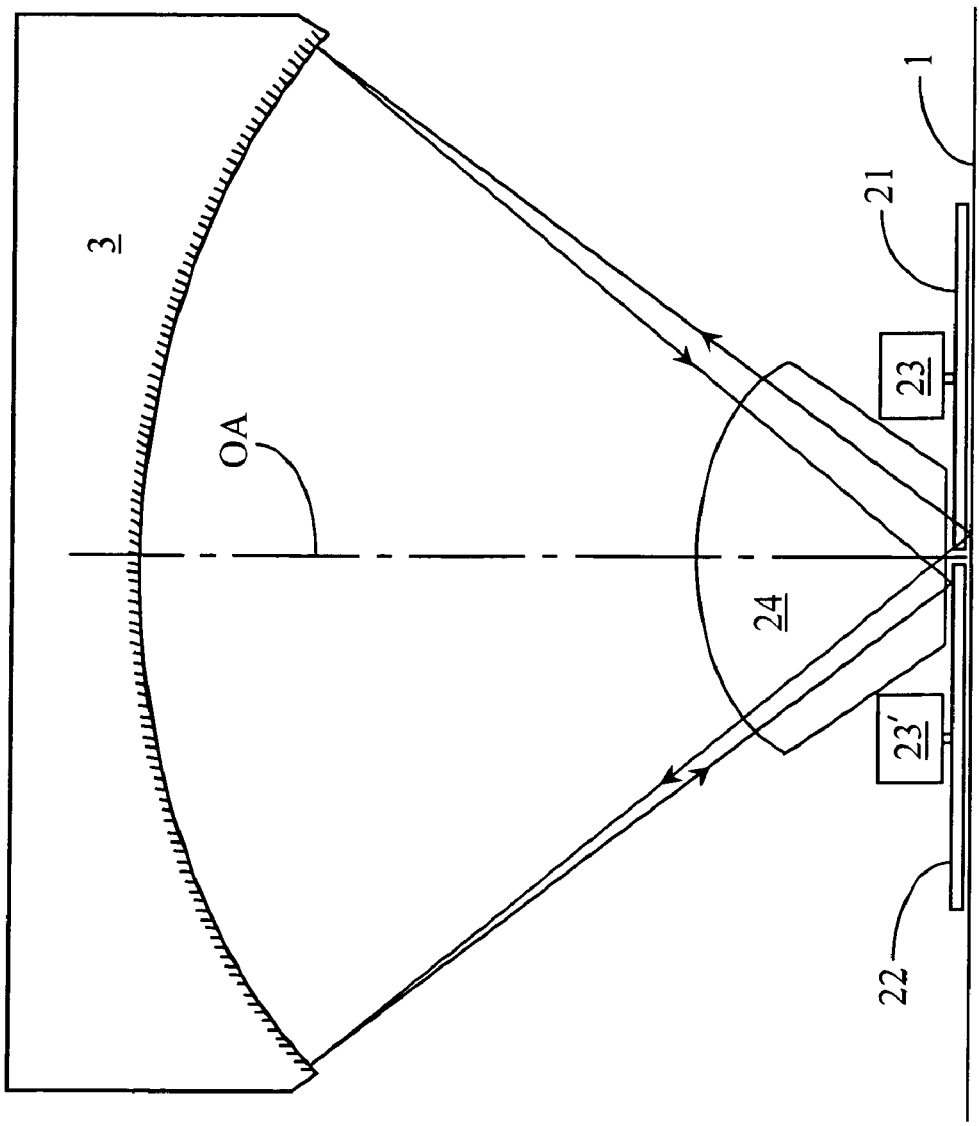
FIG. 11 depicts in cross-sectional view a Dyson optical relay, which illustrates the optical path taken by a beam passing from the substrate to the reflective grating.
Figure 12:
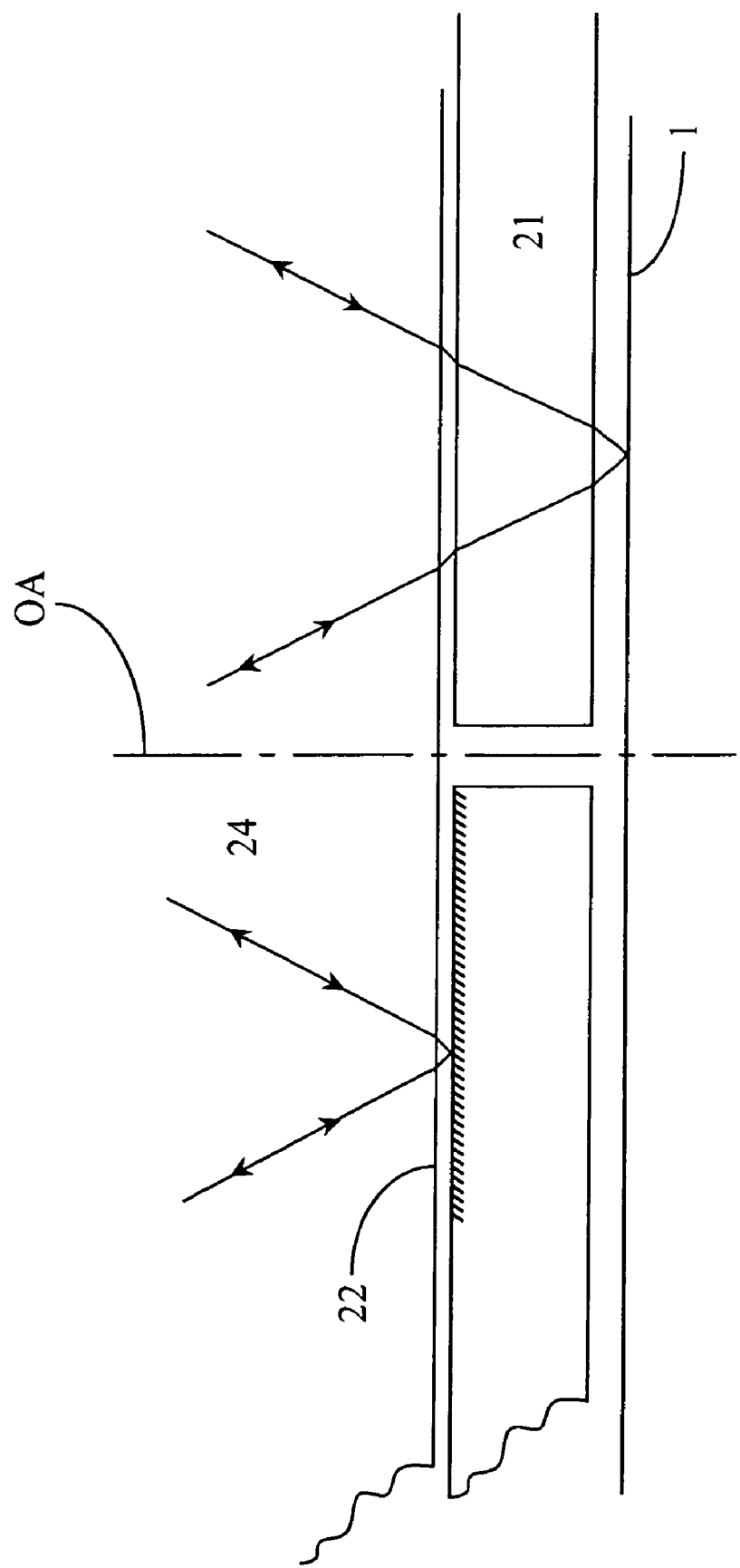
FIG. 12 depicts schematically in a highly magnified cross-section view the gap between the Dyson lens element and the substrate that shows the light path through the moving window on the object side of the relay and the light path reflected from a moving radial grating on the image side of the relay.

The all-reflective Offner system described above is ideal for recycling long wavelength radiation which tends to be either specularly reflected or absorbed and not scattered. If, however, much shorter wavelength radiation is used, such as radiation from a laser diode array operating in the near IR, the typical pattern geometries found on a semiconductor wafer may introduce appreciable scattering, and recycling this scattered radiation will require an optical system with a large NA both in and out of the plane of the incident beam. An ideal system having a very large NA is shown in FIG. 11. This is a modification of a Dyson system that ideally consists of a spherical mirror and a thick, plano-spherical lens having a radius equal to $((n-1)/n)R$ where R is the primary radius and n is the refractive index of the lens material. In the ideal system the centers of curvature of the primary and the lens are coincident and located on the plano lens surface as are the object and image planes. The modified system has a window 21 and two small air gaps between the lens 24 and the object plane 1 on one side of the optical axis OA and an air gap between the lens and the reflective grating 22 on the other side of the optical axis OA. An enlarged view of the region near the object and image planes is shown in FIG. 12.

The two main challenges with this design concept is the presence of a very hot (~1350° C.) object in very close proximity to the lens on one side of the axis and the presence of an intense reflected laser beam continually incident on the reflective grating on the other side of the optical axis. These challenges can be overcome by continuously moving both the window and the grating so the absorbed energy is spread over a large area and therefore is more easily dissipated. In FIG. 11 the grating is made as a radial grating and is spun about its axis by a motor 23 and the window is circular and is also spun about it axis by a motor 23. Thus the reflective grating can be very similar in design to that shown in FIGS. 8A and 8B. It is also possible to combine the window and grating on a single circular substrate which eliminates one of the two motors required.

The introduction of the air spaces departs from the ideal Dyson design and introduces appreciable spherical aberration, which can be largely corrected by making the primary mirror into an aspheric surface. There is also a slight departure from symmetry between the object and image sides of the system, which introduces some aberrations, however these are either very small or are cancelled when the image is relayed back to the object.

Another possible design approach is that taken by Wynne who replaced the thick lens in Dyson's design with a concentric doublet and a thick plate of higher index material to create a finite working distance. Still further improvements have been added by Hershel, who, by departing from the strict concentricity of the Wynne-Dyson design, was able to correct higher order aberrations. All of these design approaches wind-up with a thick lens near the object and image planes and a mirror spaced one focal length away from the lens. In some cases the thick lens is a composite containing multiple lens components. For convenience the refractive portion, whether it be a composite or a monolithic element, will be referred to as the "Dyson lens element".

The design parameters for a Dyson system as shown in FIG. 11 are included in the Table 2 below;

TABLE 2

| Surface | Thickness | Radius |
| --- | --- | --- |
| Substrate | 0.1 mm | |
| Window Bottom | 0.2 mm | |
| Window Top | 0.1 mm | |
| Lens Bottom | −98.508 mm | |
| Lens Top | 211.092 mm | −94.510 mm |
| Primary* | −211.092 mm | −313.381 mm |
| Lens Top | −98.508 mm | −94.510 mm |
| Lens Bottom | −0.1 mm | |
| Reflective Grating | | |

Figure 13:
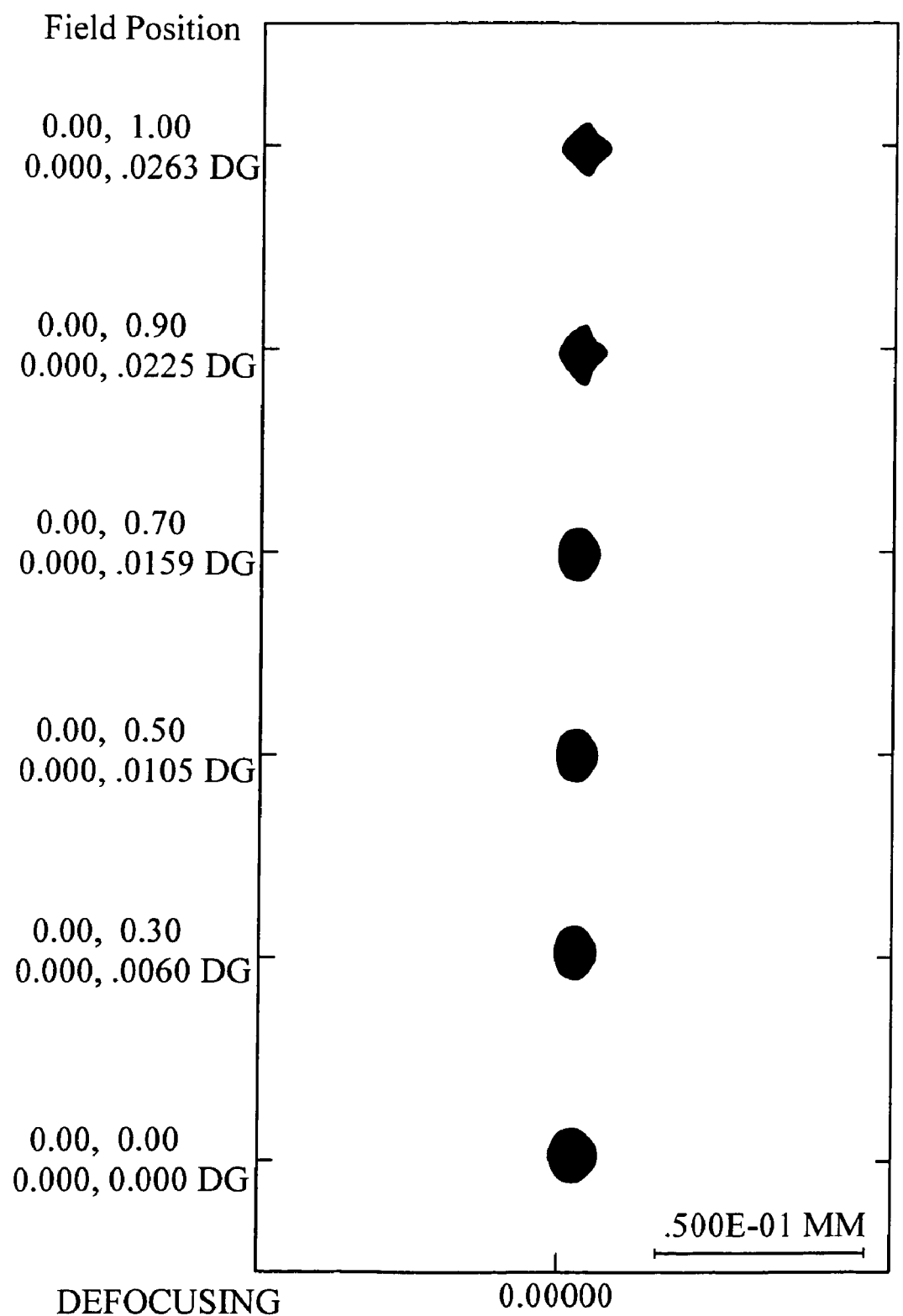
FIG. 13 illustrates the blur circle size after a beam passes from the object to the image plane in the Dyson system.

*Aspheric Constants for the Primary mirror are: $A = 0$, $B = 0$, $C = 0$, $D = 1.31884 \times 10^{-24}$, $E = -5.95739 \times 10^{-21}$, $F = 8.11005 \times 10^{-34}$, $G = 0$, $H = 0$ where the sag Z depends on the radius of curvature c and on the distance from the optical axis r as follows: $Z = cr^2/(1 + (1 - c^2r^2)^{1/2}) + Ar^4 + Br^6 + Cr^8 + Dr^{10} + Er^{12} + Fr^{14} + \ldots$ In this design it is assumed that all the refractive components are made of fused silica with an index of refraction 1.453, which corresponds to a wavelength of 800 nm, and that the maximum NA is 0.95. The field size is assumed to be 11 mm in diameter. The resulting performance shown in FIG. 13 has a maximum sized blur circle of about 18 micrometers in diameter, which is much less than the thermal diffusion distance. Also the blur circle size is amazingly constant over the entire field. Thus it should be possible to extend this design to larger field sizes and to higher NAs. The latter possibility would further increase the probability that illumination scattered from the substrate would be collected by the recycling relay and imaged back onto its point of origination after reflection from the reflective grating. If it is assumed that the scattering follows a cosine distribution, then the efficiency of the recycling system is proportional to the square of the maximum NA. Thus a 0.95 NA system might be expected to recycle 90.25% of the scattered light and a 0.98 NA system to recycle 96.04% of the scattered light.

Dyson Illuminator

Figure 14:
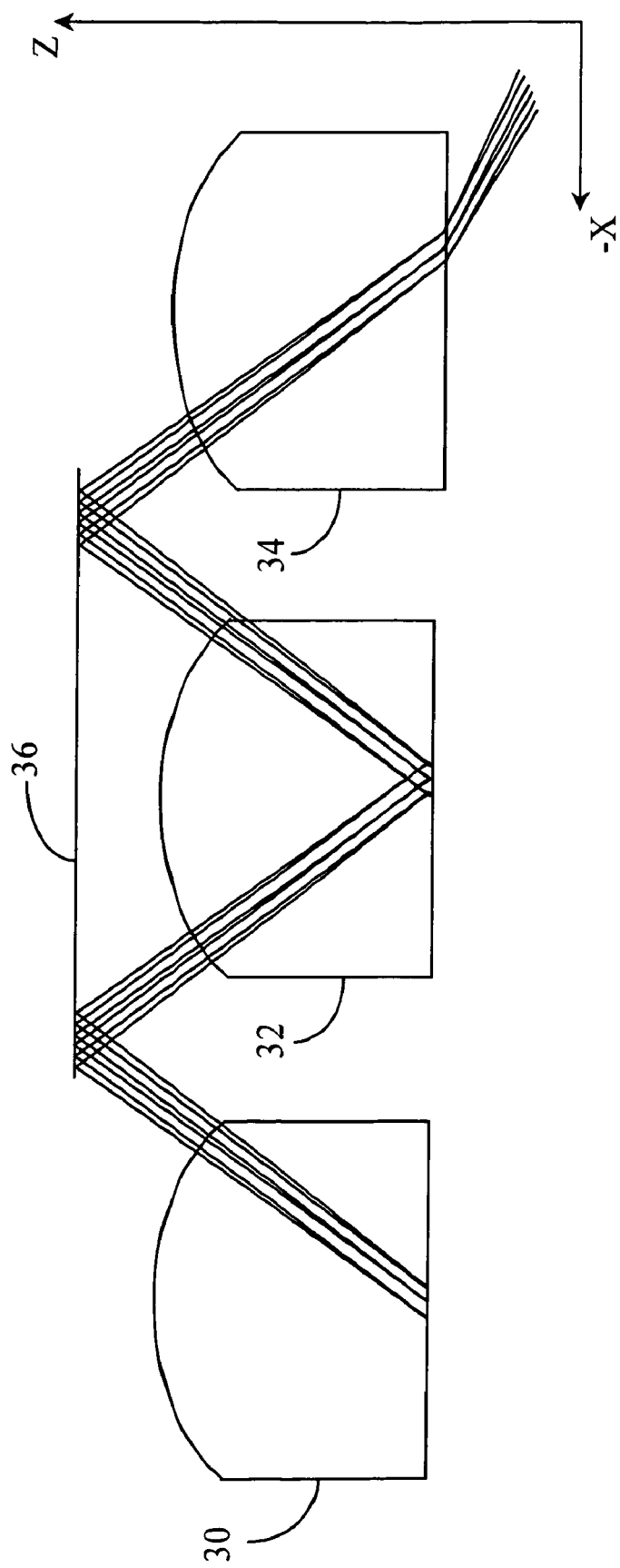
FIG. 14 illustrates an unusual off-axis design concept for an illuminator relay suitable for transferring a laser beam image onto a substrate located below a Dyson lens element in a Dyson relay.

One of the potential challenges of the Dyson recycling relay is simply getting the incident illumination onto the substrate since the Dyson lens and the moving window lie in the way. One design possibility is shown in FIG. 14 and consists of three identical plano-spherical lens elements 30, 32 and 34 each with its optical axis oriented in the z-direction and spaced apart about 190 mm in the X-direction, and a cylindrical mirror 36. In this case the plano-surface of the first element 30, which is assumed to be easily accessible, serves as conjugate image plane onto which a laser beam image can be projected at an incident angle of about 60° if it is transmitted through the plane lens surface or at 36.6° if transmitted through the spherical top surface and reflected from the plane bottom surface. This image is relayed to the center of the reflective plane surface of the intermediate Dyson element 32 after reflection from the cylindrical mirror 36 and then to the plane surface of the third Dyson element 34 after a second reflection from the cylindrical mirror 36. The third Dyson element 34 is assumed to be the Dyson lens and window combination in the Dyson recycling relay system. The relay parameters are given in Table 3 below:

TABLE 3

| Surface | Thickness | Radius |
| --- | --- | --- |
| Lens Bottom | 100 mm | |
| Lens Top | 28.762 mm | −100 mm |
| Cylindrical mirror | −28.762 mm | −257.525 mm (X-direction) −100 mm (Decentered) |
| Lens Top | −100 mm | 190 mm (Y-direction) |
| Lens Bottom | 100 mm | |
| Lens Top | 28.762 mm | −100 mm |
| Cylindrical mirror | −28.762 mm | −257.525 mm (X-direction) −100 mm (Decentered) |
| Lens Top | −100 mm | 190 mm (Y-direction) |
| Lens Bottom | | |

The index of refraction of the glass used in the Dyson elements is assumed to be 1.458467

Although the third Dyson lens element may appear redundant, it has been discovered that, with only two Dyson lens elements, the intermediate image is quite distorted (the magnification varies from one side to the other). Accordingly, three decentered Dyson lens elements are required in order to accurately convey the input distribution of energy to the substrate. The 60° incident angle of the laser illumination in this case is rather arbitrary. With this concept a wide range of incident angles is possible, provided the decentration between the Dyson elements is adjusted appropriately so the images fall near the axis of each Dyson element.

Figure 15:
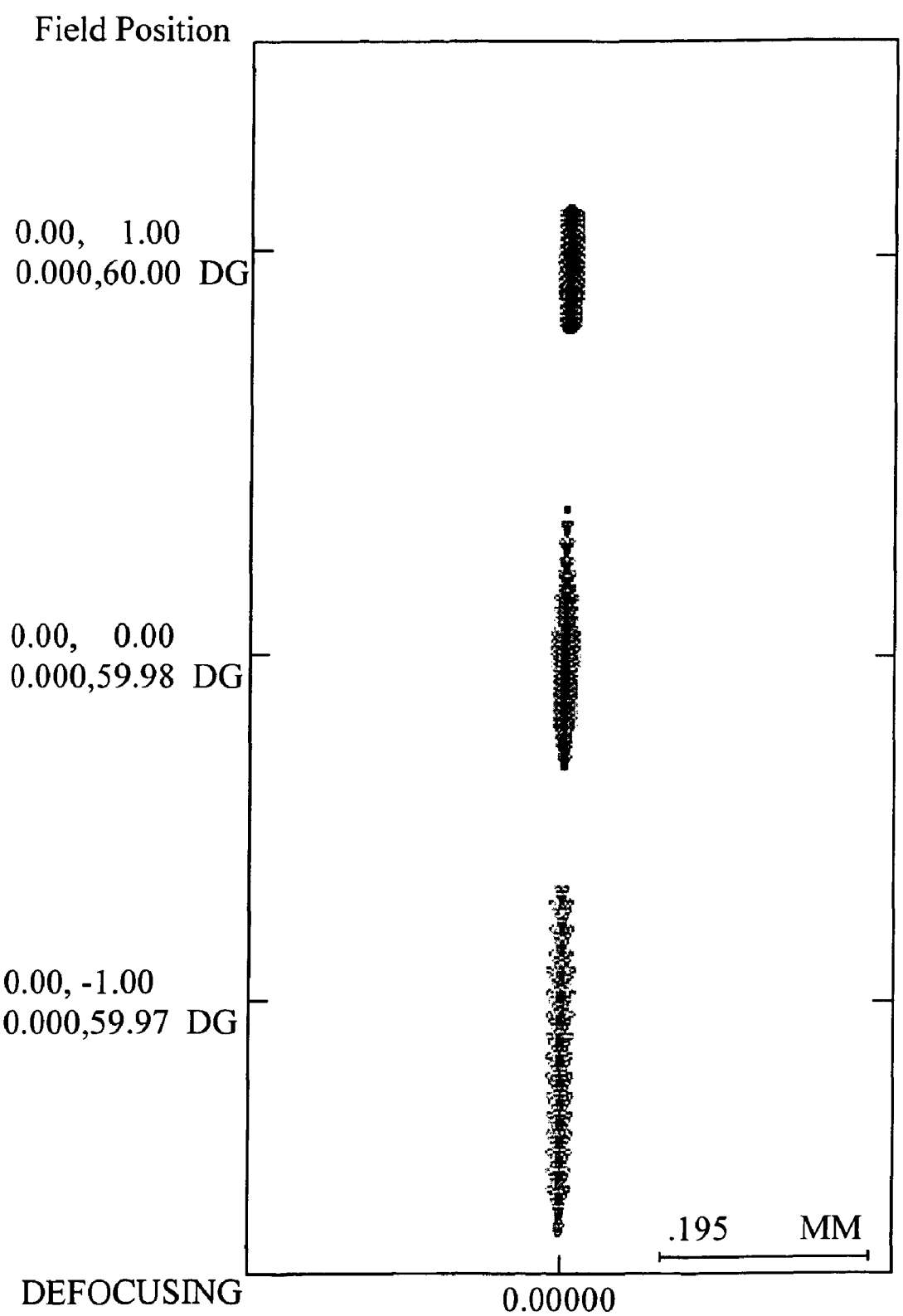
FIG. 15 illustrates the blur circle size and shape achieved using the relay design shown in FIG. 14.

The performance of the relay described in the above table is shown in FIG. 15 assuming the 0.1 NA beam incident the plane refractive surface of the first element at 60°. The blur circle images of three points spanning a 10 mm long field are astigmatic and about 18 micrometers wide and 400 micrometers long. Assuming the laser beam image is about 100 micrometers wide and about 10 mm long and is aligned with the decentration direction, the imagery provided by this rather unusual relay concept is very acceptable.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains. Furthermore, since numerous modifications and changes will readily occur to those of skill in the art, embodiments other than those of the exact construction and operation described herein are within the scope of the appended claims.

All patents and patent applications mentioned herein are hereby incorporated by reference in their entireties to an extent not inconsistent with the above description.

What is claimed is:

1. An apparatus for processing a surface of a substrate using recycled radiation, comprising:
   a radiation source positioned to direct a radiation beam toward the substrate surface at a non-normal incident angle to form a beam image thereon; and
   a recycling relay system having:
      an image field containing the beam image on the substrate surface located in an object plane,
      a conjugate image plane onto which the beam image may be projected,
      a reflective element located in the conjugate image plane,
      a pupil through which radiation may be directed, and
      a means for ensuring that radiation reflected from the reflective element is directed back toward the relay pupil and ultimately back to the substrate to recycle radiation incident on and reflected from the substrate in a +1× manner through multiple cycles without returning it to the radiation source at an intensity sufficient to interfere with the radiation source's operation.

2. The apparatus of claim 1, wherein the recycling system employs a relay having a −1× magnification ratio between the substrate and the reflective element located in the conjugate image plane.

3. The apparatus of claim 1, wherein the recycling relay system includes an Offner relay system having a ring field centered about a ring field axis.

4. The apparatus of claim 1, wherein the reflective element comprises a grating arranged to ensure that radiation reflected thereby does not return to the radiation source after a second or subsequent reflection from the substrate.

5. The apparatus of claim 3, wherein the conjugate image plane is located closer to the primary mirror than the image field.

6. The apparatus of claim 3, wherein the image field and the grating are located within the ring field of the Offner relay system.

7. The apparatus of claim 4, wherein the grating has lines pointing toward the ring field axis.

8. The apparatus of claim 7, wherein the grating is laterally translated in a direction approximately normal to the grating line direction on which the conjugate image is projected.

9. The apparatus of claim 4, wherein the grating is a radial grating that is rotatable about a central grating axis.

10. The apparatus of claim 4, wherein the grating has a groove profile that approximates a series of flat steps.

11. The apparatus of claim 4, wherein:
the grating is adapted to interact with an incident beam to form a reflected beam, the beams having chief rays that define an NA-measurement plane, and
the grating having a blaze angle equal to or larger than the arcsine of the numerical aperture of the beam from the substrate measured in the NA-measurement plane.

12. The apparatus of claim 1, wherein the recycling relay system is a Dyson system that includes small air spaces above the object and image planes and a window above the object plane.

13. The apparatus of claim 12, wherein the recycling relay system includes an aspherized primary mirror.

14. The apparatus of claim 12, wherein:
the reflective element comprises a grating, and
the window and the grating are contained in a single movable piece.

15. The apparatus of claim 14, further comprising a means for cooling the grating.

16. The apparatus of claim 12, wherein the radiation source is a laser or a laser diode.

17. The apparatus of claim 12, wherein the radiation source is a $CO_2$ laser.

18. An apparatus for processing a surface of a substrate using recycled radiation, comprising:
a radiation source positioned to direct a radiation beam toward the substrate surface at a non-normal incident angle to form a beam image thereon; and
a recycling system having:
an image field containing the beam image on the substrate surface, and
a means for collecting substantially all radiation reflected from the beam image and reimaging the collected radiation in a +1× manner back on the beam image to effectively recycle radiation incident on and reflected from the substrate through multiple cycles with a radiation loss of about 1% per cycle and without returning the recycled radiation to the radiation source at an intensity sufficient to interfere with the radiation source's operation.

19. The apparatus of claim 18, wherein the recycling system effectively recycles radiation incident on and reflected from the substrate through at least three cycles.

20. An illuminator relay in a Dyson system arrangement, comprising:
first, second, and third lens elements each having substantially identical spherical convex surfaces, plane surfaces, and lens thickness, wherein:
the convex surface has a radius that is about equal to the lens thickness,
the lens elements have a substantially identical orientation and the axis of each is parallel to the axis of the relay system, the plane surfaces of the lens elements lie in a common plane,
the lenses are displaced laterally by approximately equal distances, and
the third element serves as a refractive lens element in the Dyson system; and
a cylindrical reflective element is arranged relative to the lens elements effective to relay a uniformly illuminated field located on the center on the plane surface of the first lens element to a distorted intermediate image reflected from the plane surface of the second lens element and then to a uniformly illuminated image on or near the plane of the third lens element.

21. The relay of claim 20 in combination with a radiation source positioned to direct a radiation beam toward the plane surface of the third lens element at a non-normal incident angle to form an elongate image on the substrate, wherein:
the elongate image defines a lengthwise axis,
the lens elements are arranged along the lengthwise axis, and
the cylindrical reflective element has an axis that is parallel to a line connecting the centers of curvature for the first, second and third lens elements.

\* \* \* \* \*